(12) United States Patent
Willard et al.

(10) Patent No.: US 11,364,367 B2
(45) Date of Patent: Jun. 21, 2022

(54) MEDICAL FLUID DELIVERY

(71) Applicant: Covidien LP, Mansfield, MA (US)

(72) Inventors: Martin Willard, Burnsville, MN (US); Matthew Therrien, Maple Grove, MN (US)

(73) Assignee: COVIDIEN LP, Mansfield, MA (US)

(*) Notice: Subject to any disclaimer, the term of this patent is extended or adjusted under 35 U.S.C. 154(b) by 181 days.

(21) Appl. No.: 16/551,502

(22) Filed: Aug. 26, 2019

(65) Prior Publication Data

US 2021/0060308 A1    Mar. 4, 2021

(51) Int. Cl.
*A61M 25/09* (2006.01)
*A61M 25/00* (2006.01)
*A61M 25/02* (2006.01)

(52) U.S. Cl.
CPC ........ *A61M 25/09* (2013.01); *A61M 25/0023* (2013.01); *A61M 25/0054* (2013.01);
(Continued)

(58) Field of Classification Search
CPC .............. A61M 25/09; A61M 25/0023; A61M 25/0054; A61M 2202/0007; A61M 2025/091; A61M 2210/12; A61M 2025/0253; A61M 2025/0047; A61M 25/0045; A61M 25/0012; A61M 25/0068; A61M 25/00; A61B 2090/3966; A61B 2090/3925; A61B 2090/0811; A61B 2017/22041; A61B 17/12109; A61B 17/12186; A61B 17/00491
See application file for complete search history.

(56) References Cited

U.S. PATENT DOCUMENTS 5,234,416 A * 8/1993 Macaulay ........... A61M 25/008
                                                          600/435
5,310,407 A   5/1994 Casale
(Continued)

FOREIGN PATENT DOCUMENTS

WO        98/36790 A1    8/1998
WO        99/20326 A1    4/1999
(Continued)

OTHER PUBLICATIONS

Extended Search Report from counterpart European Application No. 20191841.4, dated Apr. 6, 2021, 11 pp.
(Continued)

*Primary Examiner* — Amber R Stiles
(74) *Attorney, Agent, or Firm* — Shumaker & Sieffert, P.A.

(57) ABSTRACT

Devices, assemblies, systems, and techniques described herein may facilitate the delivery of medical fluid, such as an adhesive, to a patient. For example, a medical assembly may include a flexible catheter configured to be disposed within an anatomical structure of a patient, wherein the flexible catheter defines a lumen configured to contain a volume of medical adhesive. The medical assembly may also include a shaft defining a shaft cross-sectional dimension smaller than a lumen cross-sectional dimension of the lumen, wherein advancement of the shaft through at least a portion of the lumen forces at least a portion of the volume of medical adhesive out of the distal opening of the lumen of the flexible catheter.

29 Claims, 16 Drawing Sheets

(52) U.S. Cl.
CPC ............... *A61M 2025/0253* (2013.01); *A61M 2025/091* (2013.01); *A61M 2202/0007* (2013.01); *A61M 2210/12* (2013.01)

(56) References Cited

U.S. PATENT DOCUMENTS

| | | | |
|---|---|---|---|
| 5,921,933 | A | 7/1999 | Sarkis et al. |
| 6,004,295 | A * | 12/1999 | Langer ............... A61M 25/0082 604/164.01 |
| 10,512,753 | B1 * | 12/2019 | Nguyen ............. A61M 25/0053 |
| 2003/0069535 | A1 * | 4/2003 | Shalaby .................. A61L 24/06 604/48 |
| 2003/0120256 | A1 | 6/2003 | Lary et al. |
| 2003/0153934 | A1 * | 8/2003 | Gerberding ....... A61M 25/0169 606/157 |
| 2006/0058737 | A1 * | 3/2006 | Herweck ............... A61M 25/00 604/164.01 |
| 2006/0095015 | A1 | 5/2006 | Hobbs et al. |
| 2010/0217306 | A1 * | 8/2010 | Raabe ................ A61B 17/1325 606/201 |
| 2015/0150863 | A1 * | 6/2015 | Wise ..................... A61M 29/00 606/191 |

FOREIGN PATENT DOCUMENTS

| | | |
|---|---|---|
| WO | 02/35986 A2 | 5/2002 |
| WO | 2010/051369 A1 | 5/2010 |
| WO | 2014/083570 A1 | 6/2014 |

OTHER PUBLICATIONS

Response to the Communication pursuant to Rules 69 and 70a(1) EPC, dated Apr. 12, 2021, from counterpart European Application No. 20191841.4, filed Oct. 8, 2021, 13 pp.

* cited by examiner

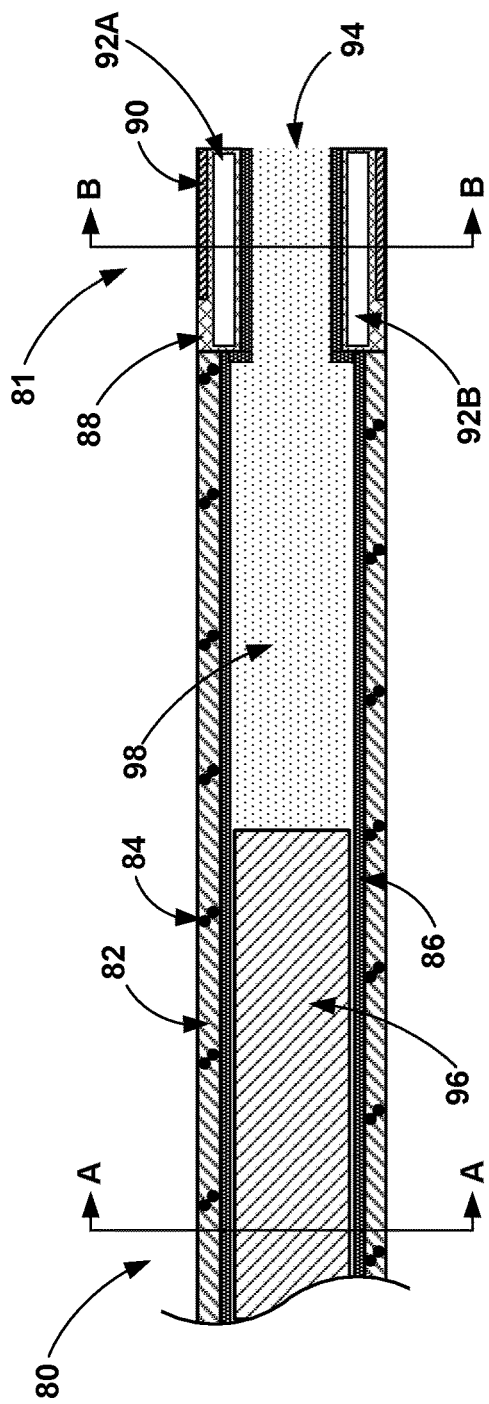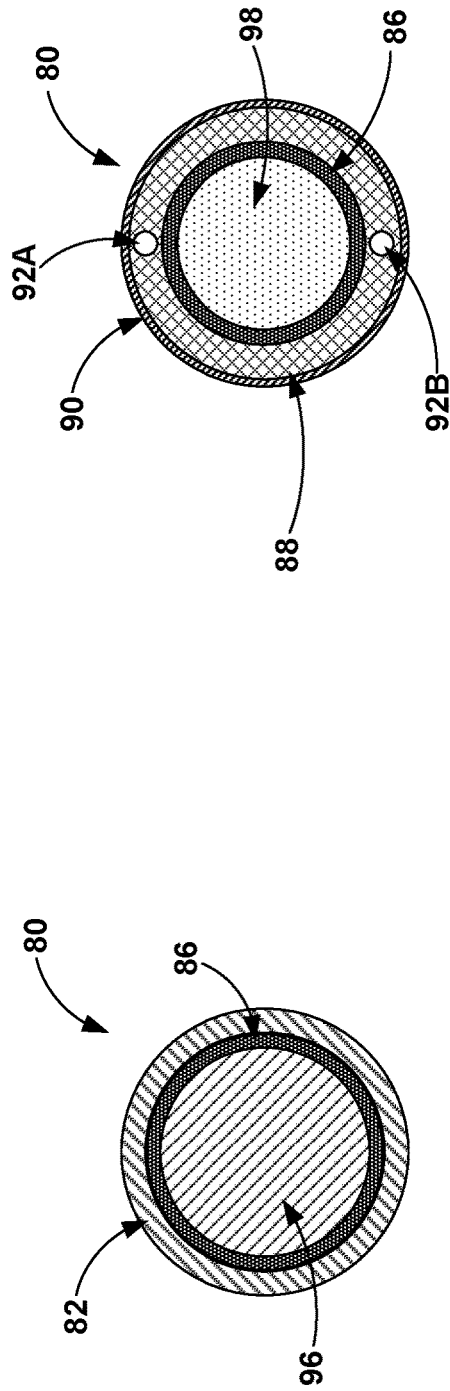
FIG. 5A
FIG. 5B
FIG. 5C

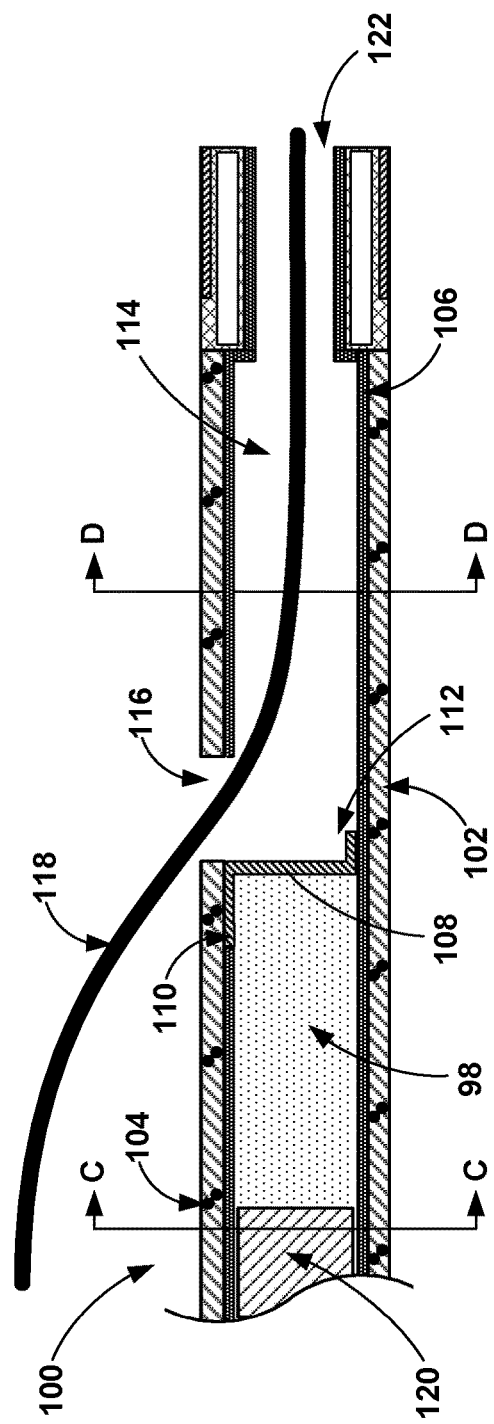
FIG. 6A
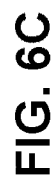
FIG. 6C
FIG. 6B

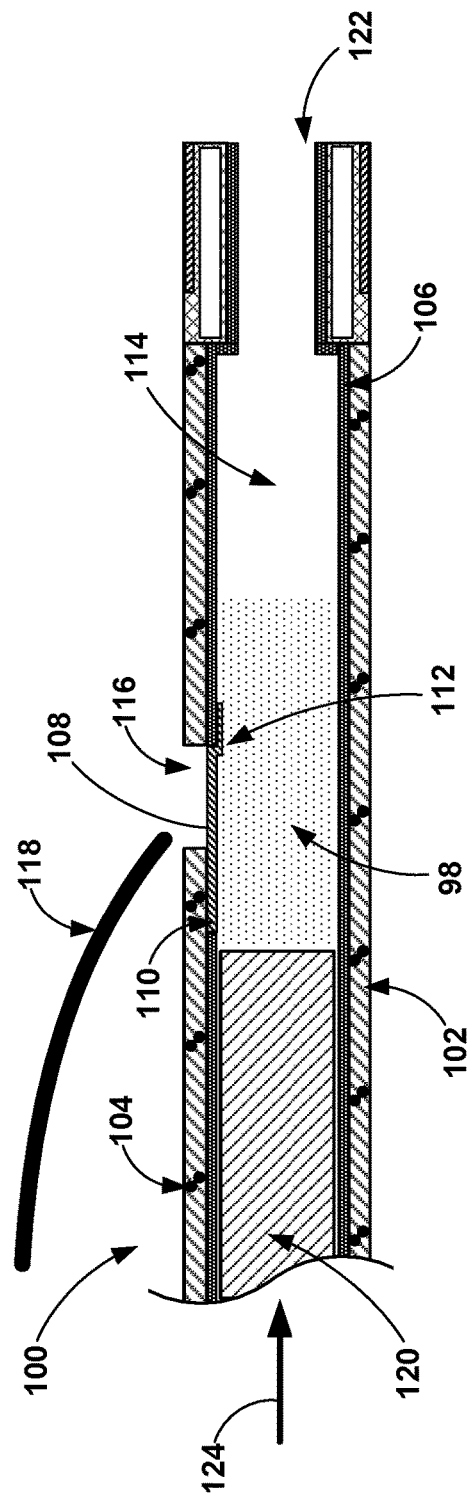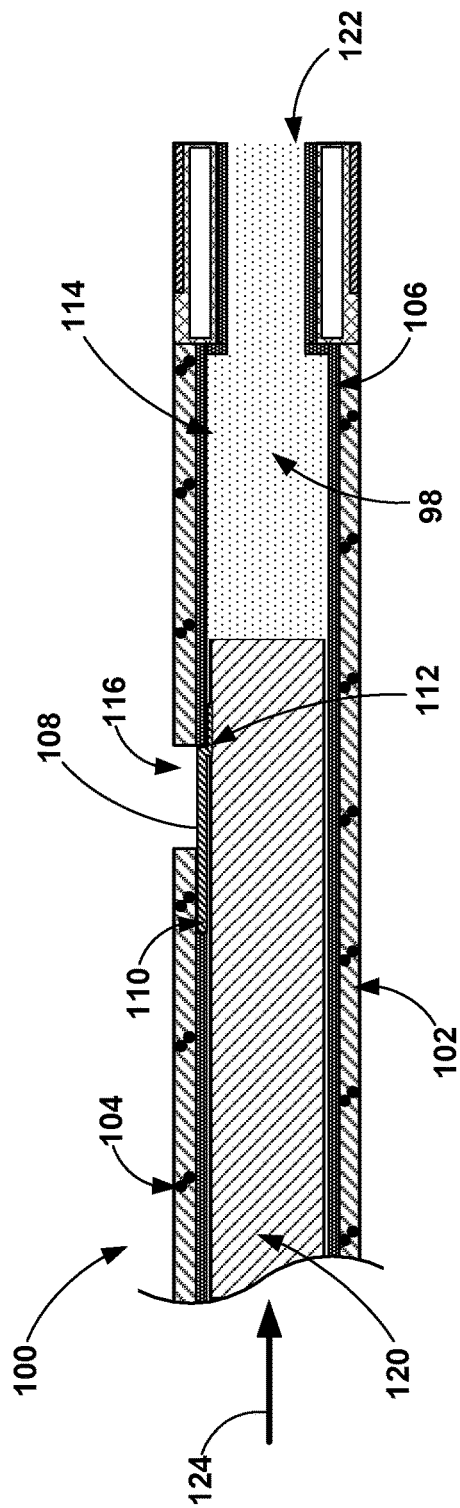
FIG. 7A
FIG. 7B

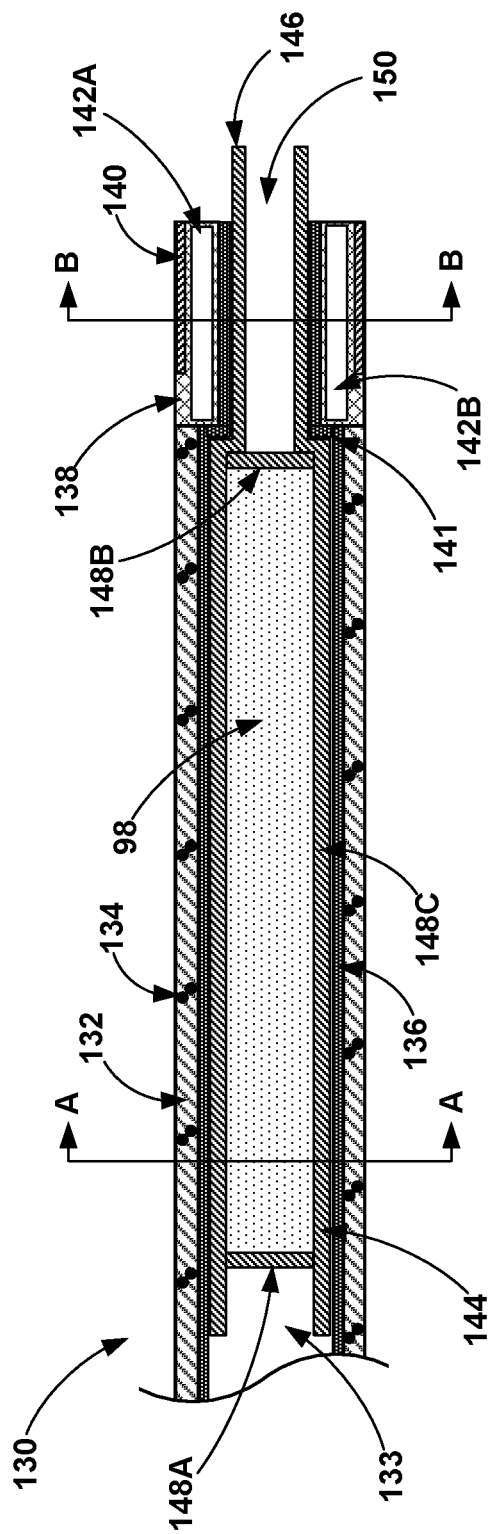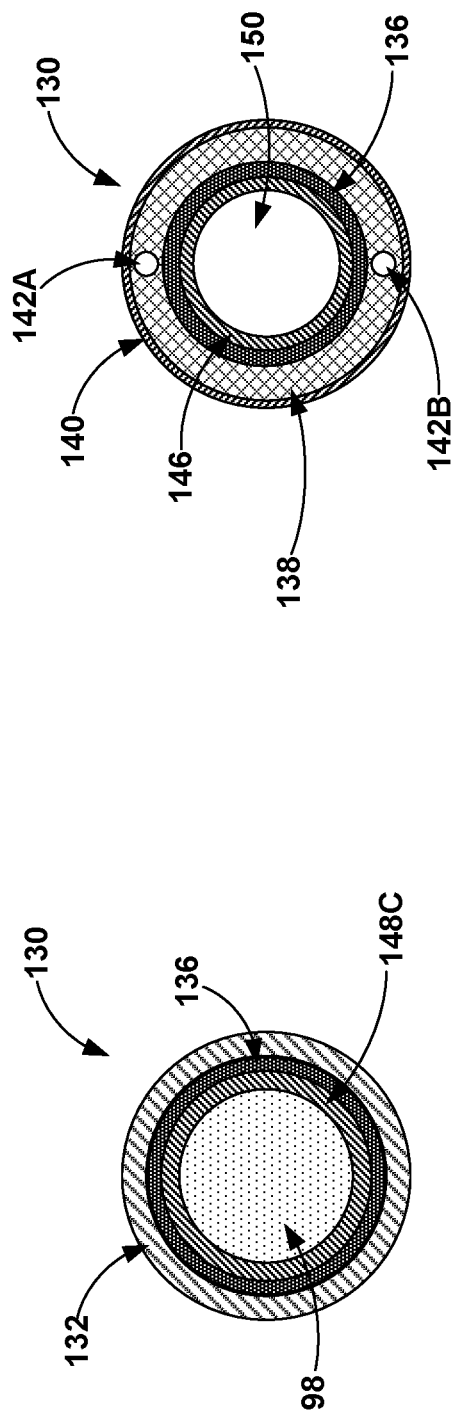
FIG. 8A
FIG. 8B
FIG. 8C

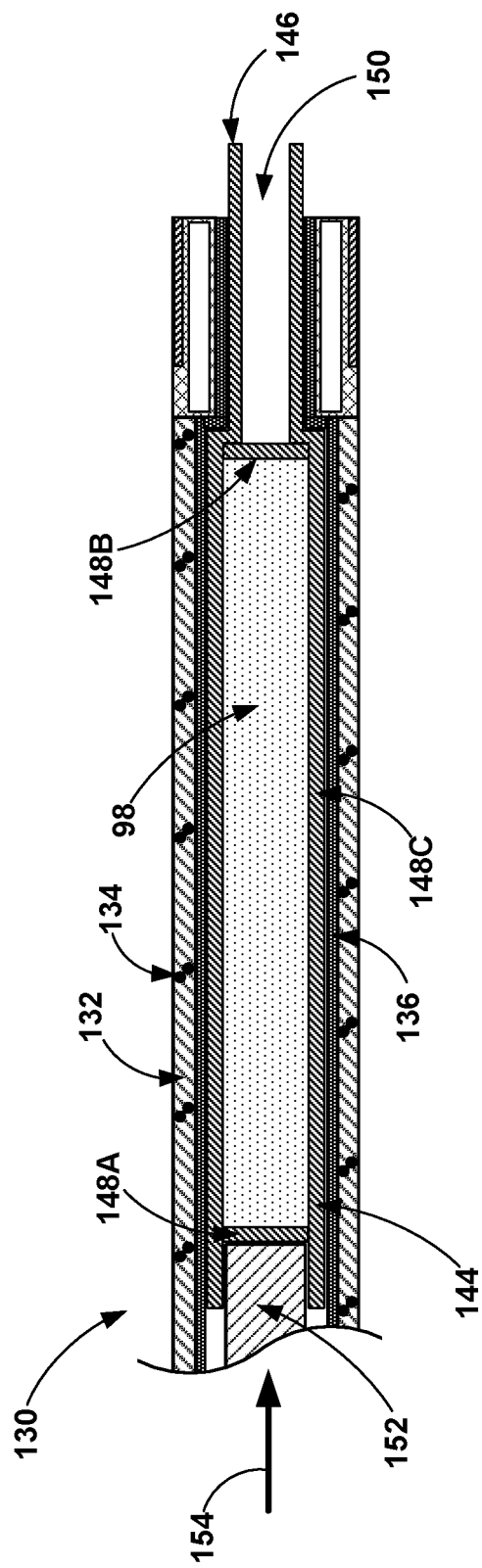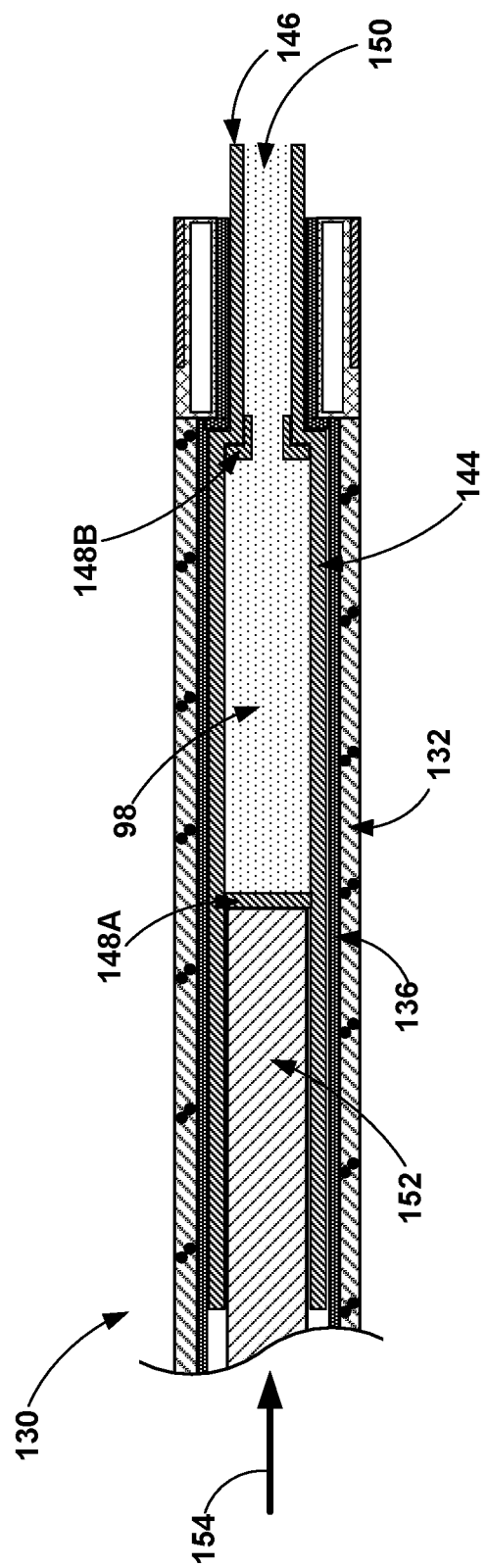

MEDICAL FLUID DELIVERY

TECHNICAL FIELD

This disclosure relates to medical assemblies and techniques for delivering fluid through a catheter.

BACKGROUND

Healthy leg veins contain valves that allow blood to move in one direction from the lower limbs toward the heart. These valves open when blood is flowing toward the heart, and close to prevent venous reflux, or the backward flow of blood. When veins weaken and become enlarged, their valves cannot close properly, which can lead to venous reflux and impaired drainage of venous blood from the legs, which may be referred to as venous insufficiency. Venous reflux is most common in the superficial veins. The largest superficial vein is the great saphenous vein (GSV), which runs from the top of the foot to the groin, where it originates at a deep vein.

Factors that may contribute to venous reflux disease include female gender, heredity, obesity, lack of physical activity, multiple pregnancies, age, past history of blood clots in the legs, and professions that involve long periods of standing. According to population studies, the prevalence of visible tortuous varicose veins, a common indicator of venous reflux disease, is up to 15% for adult men and 25% for adult women. A clinical registry of over 1,000 patients shows that the average age of patients treated for venous reflux is 48 and over 75% of the patients are women.

Venous reflux may be treated with non-invasive methods in the greater saphenous vein. Treatment modalities include radiofrequency (RF) ablation, laser endothermal ablation, and sclerotherapy, including foam sclerotherapy. One method also includes delivering an adhesive into the GSV to close off the symptomatic vein. In such adhesive treatments, the adhesive typically is taken from a sealed vial into a syringe before injected through a catheter and into the GSV.

SUMMARY

In some aspects, this disclosure describes example medical assemblies, devices, systems, and techniques for delivery of a medical fluid, such as a medical adhesive, to a patient. In one example, a medical assembly may be configured to deliver a medical adhesive to a hollow anatomical structure (e.g., a structure such as a blood vessel that is constructed to contain a fluid) to reduce blood flow or fully close the hollow anatomical structure. This closure of the hollow anatomical structure may be beneficial for treating various conditions, such as venous reflux or venous insufficiency in a superficial or deep vein of a patient. The medical assemblies described herein may be configured to deliver one or more boluses of a medical adhesive to respective locations within a hollow anatomical structure in order to seal the structure.

For example, a medical assembly may include a flexible catheter and a shaft (e.g., a mandrel) configured to be inserted within a lumen of the flexible catheter. The lumen of the flexible catheter may be pre-filled with a volume of medical adhesive. Once the flexible catheter is positioned at a target site within a hollow anatomical structure of the patient, a clinician may insert the shaft into the flexible catheter to force the medical adhesive out of the distal end of the flexible catheter and into the hollow anatomical structure for closure. In another example, the clinician may insert a pre-filled cartridge containing the medical adhesive into the lumen of the flexible catheter. Clinician insertion of the shaft into the flexible catheter may puncture through the proximal end of the pre-filled cartridge and force the medical adhesive out of the distal end of the pre-filled cartridge and out of a distal opening of the flexible catheter. In some examples, the flexible catheter may include a side opening configured to receive a guidewire that facilitates navigation of the flexible catheter to the target location within the hollow anatomical structure of the patient.

In one example, a medical assembly includes a flexible catheter configured to be disposed within a hollow anatomical structure of a patient, wherein the flexible catheter defines a lumen having a lumen cross-sectional dimension and a distal opening of the lumen, and wherein the lumen is configured to contain a volume of medical adhesive, and a shaft defining a shaft cross-sectional dimension smaller than the lumen cross-sectional dimension of the lumen, wherein advancement of the shaft through at least a portion of the lumen forces at least a portion of the volume of medical adhesive out of the distal opening of the lumen.

In another example, a method includes navigating a distal end of a flexible catheter to a target location within a hollow anatomical structure of a patient, wherein the flexible catheter defines a lumen having a lumen cross-sectional dimension, and a distal opening of the lumen, and wherein the lumen is configured to contain a volume of medical adhesive, and advancing a shaft through at least a portion of the lumen to force at least a portion of the volume of the medical adhesive out of the distal opening of the lumen, wherein the shaft defines a shaft cross-sectional dimension smaller than the lumen cross-sectional dimension of the lumen.

In another example, a medical assembly includes a flexible catheter configured to be disposed within a hollow anatomical structure of a patient, wherein the flexible catheter defines a lumen having a lumen cross-sectional dimension and a distal opening of the lumen, the lumen cross-sectional dimension comprising a range of approximately 0.102 cm to approximately 0.254 cm, the flexible catheter comprises a reinforced section comprising at least one of a coil or a braid within a wall of the flexible catheter, and the lumen is configured to contain a volume of medical adhesive, and a shaft defining a shaft cross-sectional dimension smaller than the lumen cross-sectional dimension, wherein advancement of the shaft through at least a portion of the lumen forces at least a portion of the volume of medical adhesive out of the distal opening of the lumen of the flexible catheter, wherein the volume of the medical adhesive is within a range from approximately 1.0 mL to approximately 4.0 mL.

The details of one or more examples are set forth in the accompanying drawings and the description below. Other features, objects, and advantages of examples according to this disclosure will be apparent from the description and drawings, and from the claims.

BRIEF DESCRIPTION OF THE DRAWINGS

FIG. 5A is a cross-sectional view of the distal end of an example catheter pre-filled with a vein-occluding substance and a mandrel within the catheter.

FIG. 5B is a cross-sectional view taken at A-A along the catheter of FIG. 5A, and FIG. 5C is a cross-sectional view taken at B-B along the catheter of FIG. 5A.

FIG. 6A is a cross-sectional view of the distal end of another example catheter pre-filled with a vein-occluding substance and a guidewire exit port.

FIG. 6B is a cross-sectional view taken at C-C along the catheter of FIG. 6A, and FIG. 6C is a cross-sectional view taken at D-D along the catheter of FIG. 6A.

FIGS. 7A and 7B are cross-sectional views of the example catheter of FIG. 6A and a guidewire exit port that is closed by advancement of the vein-occluding substance.

FIG. 8A is a cross-sectional view of the distal end of another example catheter configured to accept a pre-filled cartridge filled with a vein-occluding substance.

FIG. 8B is a cross-sectional view taken at A-A along the catheter of FIG. 8A, and FIG. 8C is a cross-sectional view taken at B-B along the catheter of FIG. 8A.

FIGS. 9A and 9B are cross-sectional views of the example catheter of FIG. 8A within which a mandrel forces a vein-occluding substance out of a pre-filled cartridge.

DETAILED DESCRIPTION

Figure 1A:
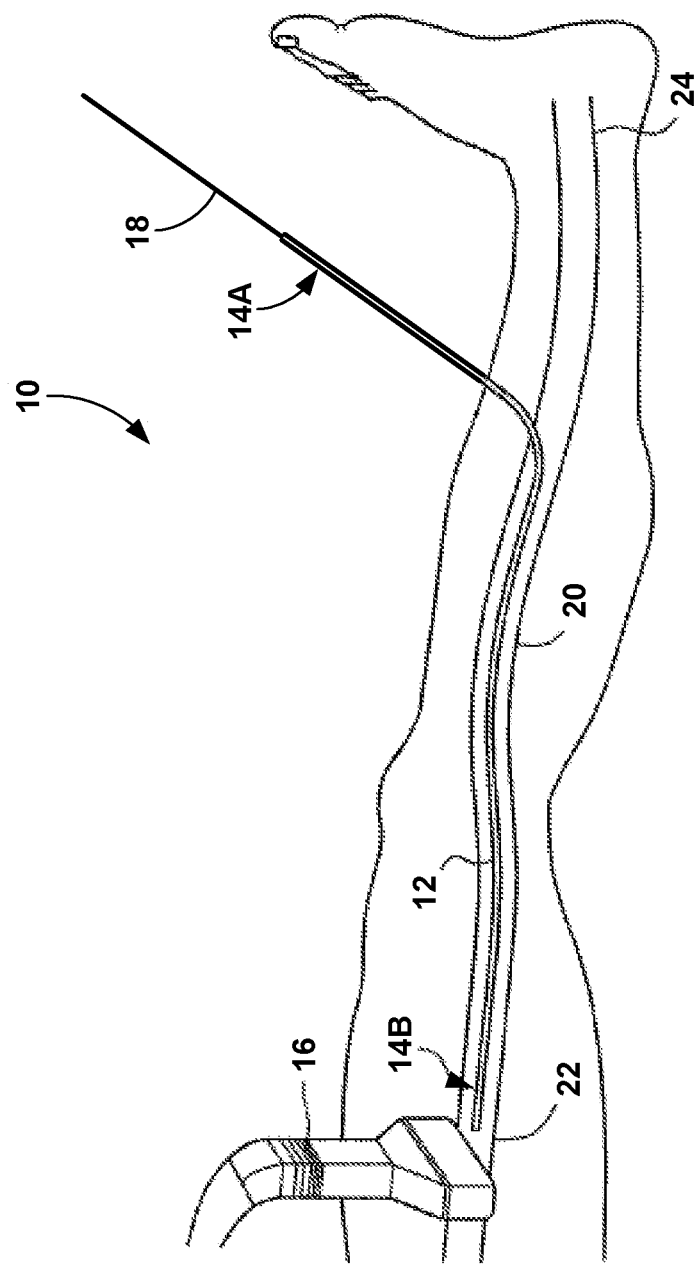
FIGS. 1A, 1B, 1C, 1D, and 1E are schematic views of an example procedure for delivering a vein-occluding substance to a patient.

This disclosure describes medical assemblies, devices, systems, and techniques related to delivering a medical fluid to a hollow anatomical structure (e.g., a vein or an artery) of a patient. Venous reflux or venous insufficiency is a condition in which valves of a vein no longer close properly and blood is able to flow backward within the vein (e.g., a greater saphenous vein or perforator vein). A treatment for venous reflux may include closure or removal of the vein or veins subject to the venous reflux. One example treatment may include delivering a medical adhesive to the vein such that the medical adhesive causes the vein to close. Once the medical adhesive cures, the introduction of adhesive prevents blood from passing through the vein. After the vein is closed, blood can reroute to other veins without compromising systemic blood flow.

An example method for delivering the medical adhesive to the vein may include use of an injector gun, a syringe, and a catheter. The medical adhesive may be stored in a container (e.g., a vial). A clinician may load the syringe with some or all of the medical adhesive contained within the vial. The clinician can then attach the catheter to the syringe, prime the catheter with the medical adhesive, insert the distal end of the catheter into the target vein, and attach the syringe to an injector gun. When the distal end of the catheter is at the target location within the vein, the clinician can actuate the injector gun which depresses the plunger of the syringe and delivers a bolus of the medical adhesive out of the distal end of the catheter. The clinician may withdraw the catheter a short distance one or more times and deliver additional respective boluses of the medical adhesive to other locations within the vein in order to achieve a complete closure of the vein.

In some examples, the medical adhesive may have a viscosity similar to honey, such as between approximately 8,000 centipoise (cps) and 12,000 cps. In some commercial adhesives, the viscosity is between 1,000 and 2,500 cps. This viscosity of the medical adhesive may provide some advantages in delivery to the vein, such as the ability to displace blood and a resistance to flowing away from the delivery location within the vein. Due to the relatively higher viscosity of the medical adhesive, the injector gun typically provides a force multiplier to enable the clinician to more easily deliver the medical adhesive from the syringe. Thus, the system requires a higher force than may be desirable to dispense the viscous medical adhesive from the syringe and through the catheter. Although the syringe and injector gun provide an effective delivery system, the system set up includes several steps prior to the procedure, which extends the procedure time and may be messy. Further, a clinician may attempt to use portions of the system, such as the syringe and medical adhesive, for the treatment of other patients, which may not be efficacious and potentially hazardous to the second patient.

In the above described method of delivering an adhesive into the GSV to close off the symptomatic vein, there may be some areas for improvement to the adhesive delivery. For example, the adhesive typically is taken from a sealed vial into a syringe, which may be time consuming and/or messy. Further, the entire length of the catheter must be primed with adhesive before adhesive may be delivered for treatment, which may also be time consuming, may waste adhesive, and may require large amounts of force to deliver depending on the viscosity of the adhesive. For at least these reasons, a system which enables a catheter to be preloaded with adhesive may be beneficial when compared to obtaining the adhesive from a sealed vial for the procedure.

Systems, devices, and techniques described herein may reduce the complexity of medical fluid delivery and promote increased patient safety. In some examples, a medical assembly may include a flexible catheter and a shaft (e.g., a mandrel) configured to be inserted within a lumen of the flexible catheter and force the medical fluid (e.g., a medical adhesive) out of a distal opening of the flexible catheter. In one example, the flexible catheter is pre-filled with a volume of medical adhesive. For example, a manufacturer may fill the flexible catheter at a manufacturing facility and store the medical adhesive within the flexible catheter such that the clinician does not need to prime the flexible catheter or otherwise transfer the medical adhesive from a storage container to the flexible catheter prior to the treatment procedure. Once the flexible catheter is inserted into a desired vein (or other anatomical structure) of the patient, the physician inserts the shaft into a proximal opening of the flexible catheter and advances the shaft through the lumen of the flexible catheter to force the medical adhesive out of the distal opening of the flexible catheter and into the vein.

In another example, the system is a cartridge-based catheter delivery system that includes a pre-filled cartridge containing a volume of the medical adhesive, separate from the flexible catheter. In one specific example, a clinician inserts the pre-filled cartridge containing the medical adhesive into the lumen of the flexible catheter. In another specific example, the pre-filled cartridge is preloaded in the lumen of the flexible catheter during manufacturing. Then, the clinician may insert the distal end of the shaft into the lumen of the flexible catheter to puncture through the proximal end of the pre-filled cartridge and force the medical adhesive out of the distal end of the pre-filled cartridge and out of the distal opening of the flexible catheter. In this manner, the shaft is advanced through the lumen of the pre-filled cartridge until the clinician has dispensed the desired amount of medical adhesive. If more medical adhesive is required than is provided in a single pre-filled cartridge, then the pre-filled cartridge may be removable from the flexible catheter and another pre-filled cartridge loaded with more medical adhesive can again be loaded into the flexible catheter. In one example, the pre-filled cartridge is filled and sealed during manufacturing. Thus, the pre-filled cartridge is provided to the clinician pre-filled and ready to be used. In another example, the cartridge is filled by the clinician (or other practitioner working with the clinician) such that the cartridge is pre-filled prior to the procedure.

The pre-filled catheter delivery system or pre-filled cartridge-based catheter delivery system may thus be configured to deliver medical adhesive without a syringe or an injector gun, which may help decrease time and cost associated with the medical procedure. Since the diameter of the flexible catheter is smaller than a syringe, less force may be required to dispense the medical adhesive from the flexible catheter compared to the syringe. These systems may also reduce the likelihood that medical adhesive would be reused for another patient because the medical adhesive is retained within the catheter that was already inserted within a patient. Reuse of the medical adhesive may be avoided to prevent the spread of disease between patients, or ensure the adhesive is efficacious, for example. The pre-filled catheter delivery system may simplify procedure setup because the medical adhesive does not need to be transferred to the flexible catheter by the clinician. The cartridge-based catheter delivery system may include a step of inserting the pre-filled cartridge (which includes the medical adhesive) into the flexible catheter prior to the procedure. The clinician may have the option of inserting another pre-filled cartridge containing additional medical adhesive if necessary to complete the closure procedure on the patient's vein.

Any of these flexible catheter delivery systems described herein may also be configured to facilitate catheter delivery using a rapid exchange guide wire. For example, the flexible catheter may include a side opening configured to receive a guidewire that facilitates navigation of the flexible catheter to the target location within the hollow anatomical structure (e.g., a vein) of the patient. Once in place, the guidewire may be removed from the lumen of the flexible catheter via the side opening. In some examples, advancement of the medical adhesive from a location proximal to the side opening may force a flap within the flexible catheter to close off the side opening to the catheter and prevent medical adhesive from exiting through the side opening. In other examples, advancement of the medical adhesive-filled cartridge distally passed the side opening may result in the pre-filled cartridge closing off the side opening in the flexible catheter that leads to the lumen defined by the flexible catheter. In other examples, the flexible catheter may have an "over-the-wire" configuration that includes a separate guide wire lumen that runs the entire length of the catheter parallel to the lumen that receives the pre-filled cartridge. In this example, the side opening and flap may not be provided.

Although the catheter delivery systems described herein are primarily described with reference to delivering a medical adhesive to a vein of a patient for purposes of treating venous reflux, these systems may be directed to treatment of other conditions or delivery of medical fluid to other locations within a patient. For example, the catheter delivery systems described herein may be configured to deliver wound closure adhesives to an injured hollow anatomical structure (e.g., a blood vessel or portion of a gastrointestinal tract) or other tissue. As another example, the catheter delivery systems described herein may configured to deliver a medical fluid, such as drug to a desired tissue of the patient. Other example uses of the catheter delivery systems described herein may include delivery of an adhesive to a specific location to interrupt blood flow, such as an arterial embolic to stop blood flow to a tumor. Although human structures are described herein, other animal species may be treated using the medical assemblies and techniques described herein.

FIGS. 1A, 1B, 1C, 1D, and 1E are schematic views of an example procedure for delivering a vein-occluding substance to a patient. As shown in FIG. 1A, medical assembly 10 includes a flexible catheter 12, with a proximal end 14A and a distal end 14B, and a shaft 18. The flexible catheter 12 has been inserted into a vein 20 of the patient. The vein 20 may be a greater saphenous vein in some examples, but the vein 20 may be any superficial, deep, or perforator vein in other examples. The vein 20 includes an inferior portion 24 and a superior portion 22. The shaft 18 (e.g., a mandrel) is inserted into the proximal end 14A of the flexible catheter 12 in order to force a portion of a medical adhesive (e.g., medical adhesive 26 shown in FIGS. 1A-1E) out of the distal end 14B of the flexible catheter 12. The shaft 18 may be inserted by the clinician or may be inserted during manufacturing and sent to the clinician pre-inserted.

The flexible catheter 12 is configured to be disposed within a hollow anatomical structure (e.g., the vein 20) of a patient. The flexible catheter 12 is an elongated structure (e.g., a tubular body) defining at least one lumen having a lumen cross-sectional dimension (e.g., a diameter in the case of a cylinder), a proximal opening of the lumen, and a distal opening of the lumen. The lumen of the flexible catheter 12 is configured to contain a volume of medical adhesive, either directly or via another structure (e.g., a pre-filled cartridge or other container) placed within the flexible catheter 12. The shaft 18 (e.g., a mandrel or other pushing member) defines a shaft cross-sectional dimension smaller than the lumen cross-sectional dimension of the lumen of the flexible catheter 12.

The shaft 18 may be an elongated structure that is axially rigid to resist compression and laterally flexible to follow curvature of the flexible catheter 12 and patient vasculature. In some examples, the shaft 18 may be constructed of a metal or metal alloy, such as medical grade stainless steel, a titanium alloy (e.g., nitinol), or any other such metal. In other examples, the shaft 18 may be constructed of a polymer or combination of polymers. The shaft 18 may have a cross-sectional shape that is at least one of circular, oval, a rounded square, or other shape. In some examples, the cross-sectional shape of the shaft 18 may be selected to correspond to the cross-sectional shape of the lumen of the flexible catheter 12 in some examples.

Advancement of the shaft 18 through at least a portion of the lumen of the flexible catheter 12 may force at least a portion of the volume of medical adhesive out of the distal opening of the lumen of the flexible catheter 12. For example, a user may apply a force to the shaft 18 in the distal direction, and the shaft 18 may transfer that force to increase the pressure of the volume of medical adhesive within the lumen of the flexible catheter 12. That increased pressure will cause at least a portion of the volume of the medical adhesive to flow distally through the lumen and eventually out of the distal end 14B of the flexible catheter 12. The shaft 18 may include a handle on a proximal end that facilitates handling from a human hand. In addition, the flexible catheter 12 may include one or more structural features near the proximal end 14A that enables a user to hold on to the flexible catheter 12 while the shaft 18 is inserted and/or advanced into the flexible catheter 12. In some examples, the flexible catheter 12 may be inserted within a lumen defined by a guide catheter. The guide catheter may be initially inserted within the vein 20 and facilitate navigation of the flexible catheter 12 to the vein 20.

In some cases, a clinician may use an imaging tool such as an ultrasound transducer 16 to assist in guiding the flexible catheter 12 to the target location(s) that will receive the medical adhesive. The ultrasound transducer 16 may be multifunctional. For example, the ultrasound transducer 16 may include one or more ultrasound sensors used to generate an image that helps a clinician guide the catheter 20 (or another device, such as a guide catheter or a guidewire) through vasculature of a patient, may serve as a compression element to the vein 20 after a bolus of medical adhesive is delivered in the vein 20, and/or identifying areas in the interior of the vein 20 that may need further occlusion or closure. In some examples, the ultrasound transducer 16 can be placed into contact with an external surface of a patient's skin prior to placing the flexible catheter 12 or any other devices (e.g., an introducer catheter or guidewire through vessel 20). The ultrasound transducer 16 can assist in generating images to help guide one or more catheters or guide devices to the target site or sites where a vein-occluding substance (e.g., a medical adhesive) will be introduced. In some examples, the ultrasound transducer 16 can also serve as a compression element prior to, during or after introducing the medical adhesive to assist in closure of the vein 20. By serving as a compression element, the ultrasound transducer 16 can help to flatten and/or reduce the size of the vein 20. In some examples, the ultrasound transducer 16 can include a Doppler flow detection capability, and help to identify areas in the interior of the vein 20 that may need further closure or occlusion and thus, further application of a vein-occluding sub stance.

In some examples, the flexible catheter 12 may include one or more features that promote visualization of one or more portions of the flexible catheter 12 under ultrasound visualization with the ultrasound transducer 16. For example, the flexible catheter 12 may include one or more echogenic portions at the distal portion of the flexible catheter 12. The echogenic portion may include one or more cavities defined in the wall of the flexible catheter 12. These cavities may be disposed circumferentially, axially, and/or or radially within the wall of the flexible catheter 12. The cavities may include a gas (e.g., air or nitrogen), a solid material (e.g., a metal alloy), or some other material that can be differentiated from other anatomical structures or fluids within the patient.

Figure 1B:
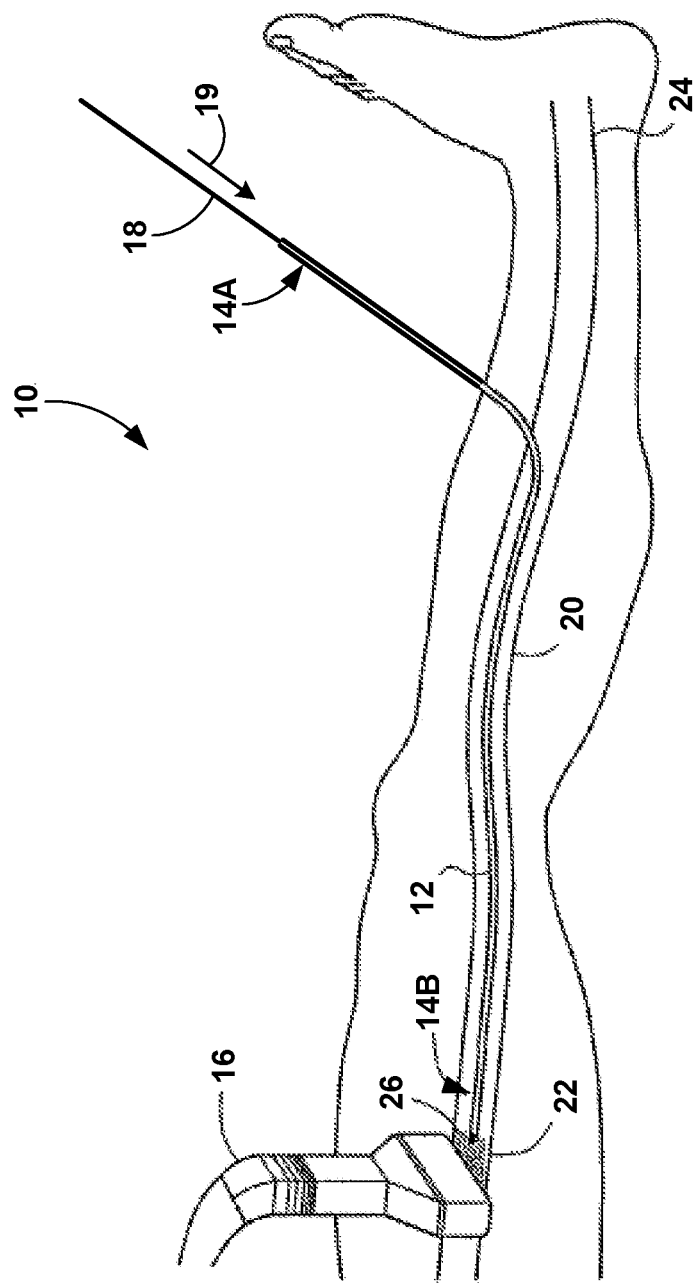

As shown in FIG. 1B, advancement of the shaft 18 in the (distal) direction of arrow 19 may apply a force to the volume of medical adhesive contained within the flexible catheter 12 that displaces the bolus 26 of the medical adhesive out of distal end 14B of the flexible catheter 12. In some examples, the shaft 18 may include one or more markings along the length of the shaft 18 that indicate the volume of medical adhesive delivered by advancement of the shaft 18. For example, each marking along the length of the shaft 18 may specify a single bolus or some specified volume, such as 0.2 milliliters (mL) or some other volume increment. In this manner, the user may use the markings along the shaft 18 in relation to the proximal opening of the flexible catheter 12 as a measurement of the amount of volume of the medical adhesive delivered during advancement of the shaft 18.

Figure 1C:
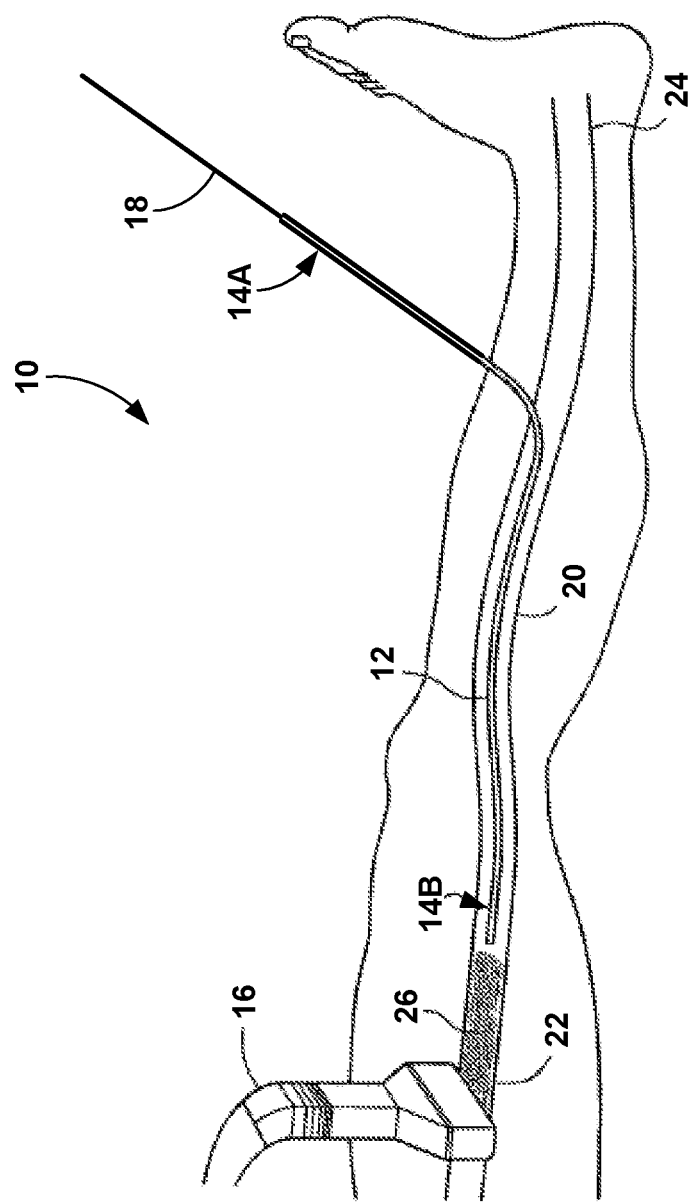
Figure 1D:
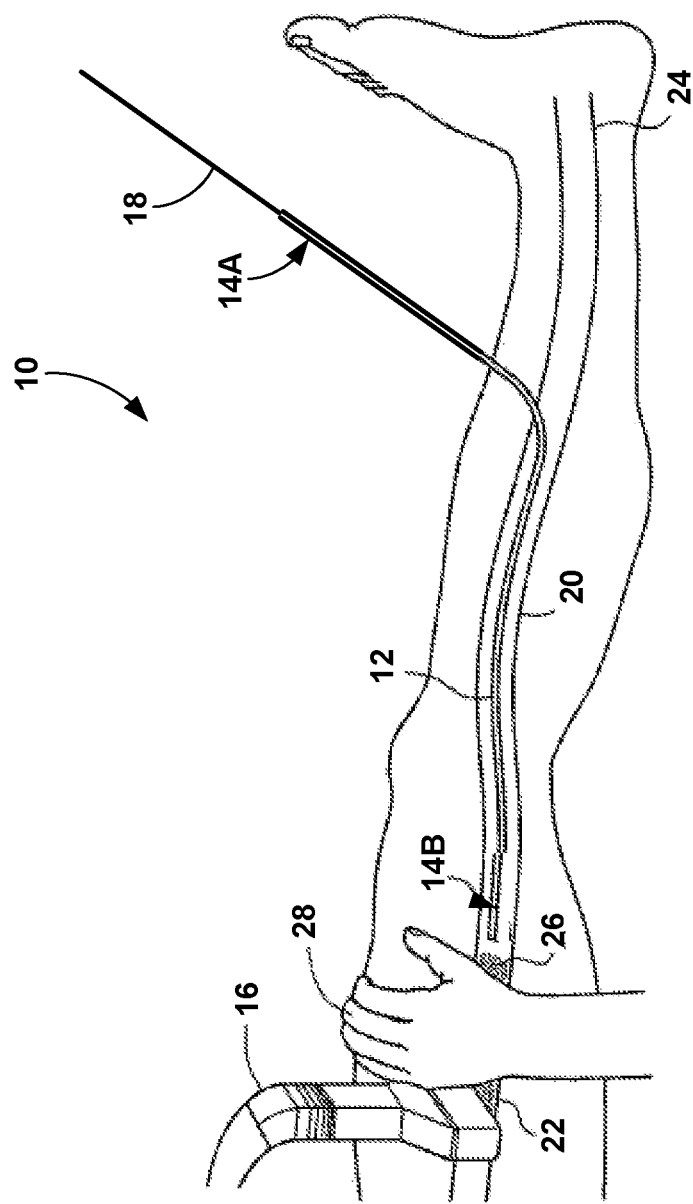

In the example of FIG. 1C, the bolus 26 of the medical adhesive has been delivered into the vein 20 and the clinician has proximally withdrawn the flexible catheter 12 from the site at which the bolus 26 was delivered. Once the flexible catheter 12 is removed from the area containing the bolus 26, the clinician may apply pressure to that portion of the vein 20 with the medical adhesive of the bolus 26. For example, as shown in FIG. 1D, an optional compression element, e.g., an operator's hand 28, a sequential compression device, or the ultrasound transducer 16 can be used to apply pressure on the external surface of the patient's body and compress the interior walls of the vein 20. The optional compression element can be used to compress portions of the vessel prior to, during or after the introduction of the medical adhesive. When the compression element compresses portions of the vein 20 during or after the introduction of the bolus 26, the vessel is compressed against the bolus 26, as shown in FIG. 1D. This compression assists in occlusion as well as collapse of the vein 20 in order to coapt the vessel walls. In some examples, as additional portions of the vessel are treated with the medical adhesive, the target regions of the vein 20 can be compressed immediately following, or no more than about 5 minutes, 4 minutes, 3 minutes, 2 minutes, 1 minute, 30 seconds, 15 seconds, or less following injection of the medical adhesive.

After delivering of the bolus 26 and application of pressure to the site containing the bolus 26, the clinician may withdraw the flexible catheter 12 to a new location within the vein 20 and repeat the process shown in FIGS. 1B-1D in order to deliver another bolus of the medical adhesive to the new location within the vein 20. In some examples, different locations for delivery of the medical adhesive may be spaced apart between approximately 0.5 centimeters (cm) and approximately 5 cm along the length of the vein 20. In other examples, the distal end 14B of the flexible catheter 12 may be moved between approximately 3% to approximately 50% of a total length of the vein 20 to be treated for each location to receive a bolus of the medical adhesive. In some examples, each site for treatment may be between approximately 3% to approximately 20% of the total length of the treatment site for the vein 20. In some examples, the total treatment site of the vein 20 may have a length between approximately 2 cm and approximately 50 cm, or between approximately 5 cm and approximately 40 cm in some examples.

Figure 1E:
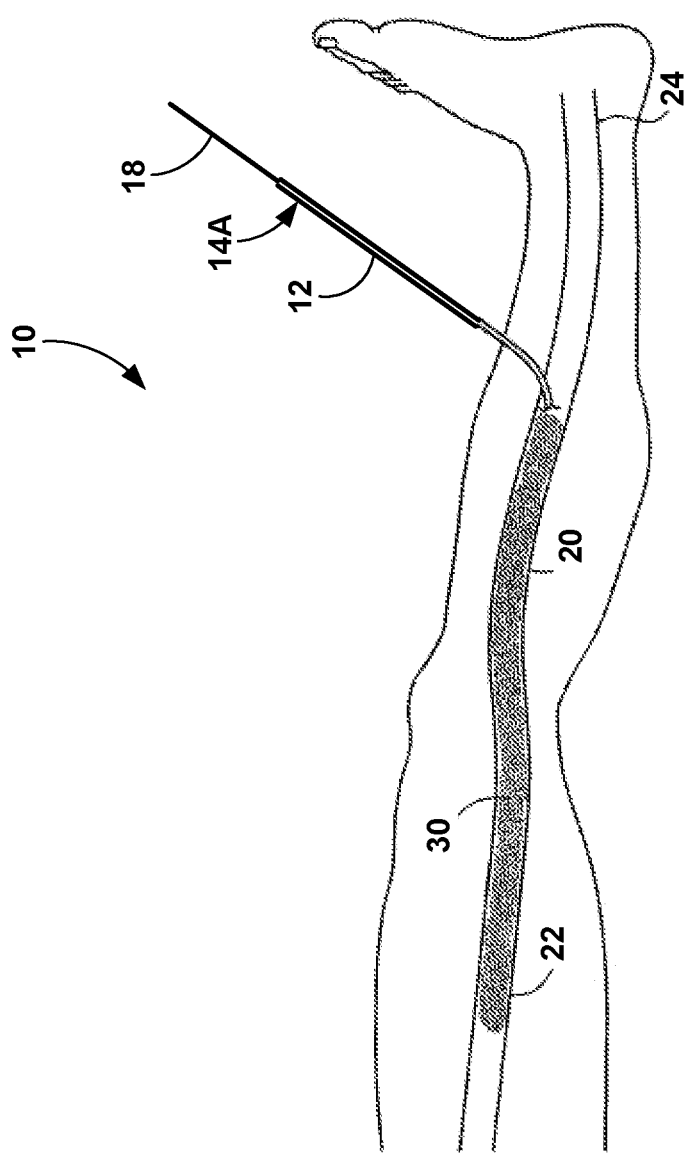

As shown in FIG. 1E, multiple boluses of the medical adhesive have been delivered to the vein 20 in order to create an occluded portion 30 of the vein 20. The occluded portion 30 may include medical adhesive that has been delivered from the catheter 12 and into the vein 20 and adhered to the walls of the vein 20. In some examples, the occluded portion 30 may include a continuous length of medical adhesive caused by multiple delivered boluses. In other examples, the occluded portion 30 may include multiple separate areas of the vein 20 that have been coapted by the medical adhesive. After the medical adhesive is delivered, the clinician may remove the flexible catheter 12 and the shaft 18 from the vein 20 and the patient.

In some examples, such as the examples of FIGS. 5A-7B, the lumen of the flexible catheter 12 is pre-filled (e.g., filled by a manufacturer as opposed to being filled by the clinician) with a volume of the medical adhesive. The volume of medical adhesive pre-filled in the lumen may be sufficient to treat an entire length of the vein 20. By pre-filling the flexible catheter 12 with the volume of the medical adhesive, a user will not need to add the medical adhesive to the flexible catheter 12 prior to performing the procedure on the patient. In some examples, the proximal end 14A of the flexible catheter 12 may be sealed or a plug may be inserted proximal to the medical adhesive in the lumen in order to seal the lumen of the flexible catheter 12 and prevent the medical adhesive from curing when stored within the flexible catheter 12. In addition, a seal, membrane, or cap may be provided on the distal end 14B of the flexible catheter 12 to preserve the medical adhesive in the uncured stated while stored within the flexible catheter 12. A user may remove the proximal or distal seal prior to use, or in some examples, advancement of the shaft 18 may puncture or displace the proximal seal, while pressure caused by the advancement of the shaft 18 may rupture the distal seal. In this manner, the device or mechanism provided to seal the medical adhesive within the flexible catheter 12 may be configured to be removed, displaced, or ruptured by advancement of the shaft 18 within the lumen of the catheter 12.

When the lumen of the flexible catheter 12 is pre-filled with a volume of medical adhesive, the cross-sectional dimension of the shaft 18 may be sized to correspond with the cross-sectional dimension of the lumen of the flexible catheter 12. For example, the cross-sectional dimension (e.g., a diameter for a cylindrical shaft) of the shaft 18 may be slightly smaller than the cross-sectional dimension of the lumen of the flexible catheter 12 to enable the shaft 18 to move within the lumen but prevent much, if any, medical adhesive from passing between the shaft 18 and the wall of the flexible catheter 12. Therefore, the diameter of the shaft 18 may not be exactly the same as the diameter of the lumen defined by the flexible catheter 12. In some examples, a distal end of the shaft 18 may include, be attached to, or otherwise be in contact with a movable plug that separates the medical adhesive from the shaft 18. In this manner, the shaft 18 may force the movable plug against the medical adhesive to force the medical adhesive out of the distal end 14B of the flexible catheter 12.

In some examples, the flexible catheter 12 may be configured to be inserted into the vein 20 or other hallow anatomical structure over a guidewire. The guidewire may first be inserted into the vein 20 and then the flexible catheter 12 may be inserted over the guidewire until the distal end 14B is located at the desired location. When the flexible catheter 12 is pre-filled with the medical adhesive, the guidewire must be able to pass out from the lumen of the flexible catheter 12 and through the wall of the flexible catheter 12 at a location distal to where the medical adhesive is contained within the flexible catheter 12. In some examples, the flexible catheter 12 may define a side opening in the wall of flexible catheter at a location distal to the volume of the medical adhesive pre-filled within the lumen, the side opening being sized to accept a guidewire. The wall of the flexible catheter 12 may define a side opening that is circular, ovular, square, rectangular, or any other shape that is configured to receive the guidewire.

A structure, such as a flap, may be disposed within the flexible catheter 12 to retain the medical adhesive proximal to the side opening when the guidewire is inserted within the lumen of the flexile catheter 12. Once the guidewire is removed, the structure may be moved to enable delivery of the medical adhesive through the lumen of the catheter 12 and distal to the structure. For example, the flexible catheter 12 may include a flap that is configured to move between a first position that retains the volume of the medical adhesive proximal to the side opening and a second position that closes the side opening from the lumen and enables the adhesive to move past the side opening. In some examples, advancement of the medical adhesive distally within the lumen of the flexible catheter 12 (e.g., via advancement of the shaft 18) forces the flap from the first position to the second position. In the second position, the flap enables the medical adhesive to flow through the lumen and distal to the side opening.

In other examples, such as the examples of FIGS. 8A-10B, the lumen of the flexible catheter 12 is configured to accept a pre-filled cartridge filled with the volume of the medical adhesive. The pre-filled cartridge is configured to be inserted at least partially into the lumen of the flexible catheter 12. The pre-filled cartridge may define an outer diameter that corresponds to the lumen cross-sectional dimension of the lumen of the flexible catheter 12. The outer diameter of the pre-filled cartridge may be slightly smaller than the diameter of the lumen of the flexible catheter in order to enable the pre-filled cartridge to slide within the lumen. In some examples, the cross-sectional dimension of the shaft 18 is sized to enable the shaft 18 to slide within the lumen defined by walls of the pre-filled cartridge. In these examples, advancement of a distal end of the shaft 18 through a proximal portion of the pre-filled cartridge forces at least a portion of the medical adhesive out of the distal end of the pre-filled cartridge and out of the distal opening of the lumen of the flexible catheter 12. In other examples, the shaft 18 may contact and compress the sidewall of the pre-filled cartridge as the shaft 18 is advanced distally within the lumen of the flexible catheter 12 in order to expel the medical adhesive out of the pre-filled cartridge and the distal opening of the flexible catheter 12.

In some examples, the flexible catheter 12 that is configured to accept the pre-filled cartridge filled with medical adhesive also defines a side opening sized to accept a guidewire that facilitates navigation of the flexible catheter 12 to the target location within a patient. After positioning the flexible catheter 12 at the target location, the guidewire may be removed from the lumen of the catheter 12. Then, the pre-filled cartridge may be advanced distally within the lumen of the flexible catheter 12 until the distal end of the pre-filled cartridge is distal to the side opening, such that the pre-filled cartridge covers the side opening and closes the side opening. In some examples, the flexible catheter 12 may include a flap configured to move between a first position that enables the guidewire to enter the side opening defined by the catheter 12 and a second position that closes the side opening from the lumen of the catheter 12. Advancement of the pre-filled cartridge distally within the lumen of the flexible catheter 12 forces the flap from the first position to the second position. In some examples, the flap may be constructed of a more resilient material than the wall of the pre-filled cartridge. The wall of the pre-filled cartridge may bulge or burst at the side opening when subjected to the pressures applied by the shaft 18. The flap may thus provide support for the wall of the pre-filled cartridge at the side opening and help ensure that medical adhesive is directed out of the distal opening of the flexible catheter 12.

The lumen of the flexible catheter 12 may generally have a cross-sectional dimension in a range of approximately 0.040 inches (in) (0.102 centimeters (cm)) to approximately 0.100 in (0.254 cm). The external dimension (e.g., the external diameter) of the flexible catheter 12 may be in a range of approximately 0.045 in (0.114 cm) to approximately 0.115 in (0.292 cm). These sizes may correspond to flexible catheter 12 having a French sizing from a 3 French to a 9 French diameter. However, smaller or larger diameters may be used in other examples. The flexible catheter 12 may be constructed of one or more polymer layers, and in some examples, the polymers may change along the length of the flexible catheter 12. In some examples, the flexible catheter 12 may include a reinforced section comprising at least one of a coil or a braid within a wall of the flexible catheter 12 (e.g., embedded within the wall). The coil or braid may be constructed of a polymer or one or more metals. In some examples, the flexible catheter 12 may include a polytetrafluoroethylene (PTFE) liner that defines the lumen that contains the medical adhesive or is configured to accept a pre-filled cartridge that contains the medical adhesive.

In some examples, the medical adhesive described herein may have a viscosity between approximately 8,000 centipoise (cps) and 12,000 cps. In other examples, the medical adhesive may have a viscosity between 1,000 cps and 2,500 cps. The volume of medical adhesive pre-filled in the flexible catheter 12 or contained within a single pre-filled cartridge may be within a range from approximately 1.0 mL to approximately 4.0 mL. This volume may be selected based on target vessels to be treated (e.g., the greater saphenous vein may require a larger volume of medical adhesive than a perforator vein). Each bolus of medical adhesive delivered to a single location within the vessel may be in a range of approximately 0.01 cubic centimeters (cc) to 3 cc. In one example, each bolus may be in a range of approximately 0.01 cc to 1.0 cc of medical adhesive.

Example medical adhesives may include cyanoacrylate (e.g., 2-octyl cyanoacrylate). In some examples, a cyanoacrylate can be an aliphatic 2-cyanoacrylate ester such as an alkyl, cycloalkyl, alkenyl or alkoxyalkyl2-cyanoacrylate ester (e.g., VenaSear™, Medtronic, Minneapolis, Minn.). The alkyl group may have from 1 to 16 carbon atoms in some embodiments, and can be a C1-C8 alkyl ester or a C1-C4 alkyl ester. Some possible esters include the methyl, ethyl, npropyl, isopropyl, n-butyl, isobutyl, pentyl, hexyl, cyclohexyl, heptyl, octyl, 2-methoxyethyl and 2-ethoxyethyl esters of cyanoacrylic acid. Other medical adhesives that can be used include a biological glue such as a bovine serum albumin-gluteraldehyde combination (e.g., BIOGLUE, Cryolife, Atlanta, Ga.), PVA, Biogard, collagen, fibrinogen, fibronectin, vitronectin, laminin, thrombin, gelatin, mixtures thereof, or other biocompatible adhesives.

The flexible catheter 12 may deliver other fluids in other examples. Materials other than adhesives may be used, including a sclerosing agent such as hypertonic saline, sodium tetradecyl sulfate, chromated glycerol, tetracycline, talc, bleomycin, or polydocanol. For example, a foam generated from, for example, one or more of the above components can be used to enhance ablation and closure of the vein 20. The viscosity and air bubble mixture can also be controlled while taking into account the desired clinical result. In some examples, the cyanoacrylate preparation contains one or more additives that impart the desired properties to the preparation as viscosity, color, radioopacity, and the like. Certain examples of additives such as thickening agents and polymerization inhibitors are discussed further below.

In some examples, the adhesive can also include a therapeutic agent such as an anti-inflammatory agent, an anti-infective agent, an anesthetic, a pro-inflammatory agent, a cell proliferative agent, or combinations thereof. In some examples, the medical adhesives, such as the cyanoacrylate adhesives, can have select properties. In some examples, the medical adhesives can have a setting time of between about 5 to 60 seconds, or less in some examples. The setting time may be almost instantaneous with blood contact in other examples.

FIGS. 2A, 2B, 2C, 2D, and 2E are conceptual views of an example procedure for delivering a vein-occluding substance, such as a medical adhesive, to a patient at multiple target locations. The procedure of FIGS. 2A-2E may be similar to FIGS. 1A-1E. However, FIGS. 2A-2E describe a procedure in which the medical adhesive adheres to an occlusion formed in a vein 44, which is an example of the vein 20 described with reference to FIGS. 1A-1E. The flexible catheter 40 may be similar to the flexible catheter 12 of FIGS. 1A-1E.

Figure 2A:
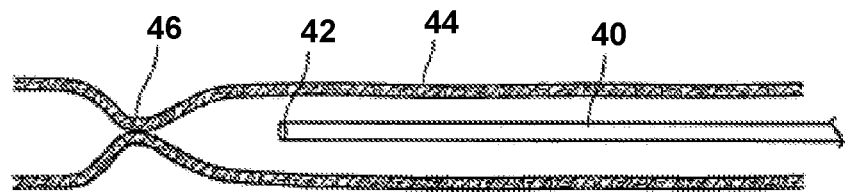
FIGS. 2A, 2B, 2C, 2D, and 2E are schematic views of an example procedure for delivering a vein-occluding substance to a patient at multiple target locations.
Figure 2B:
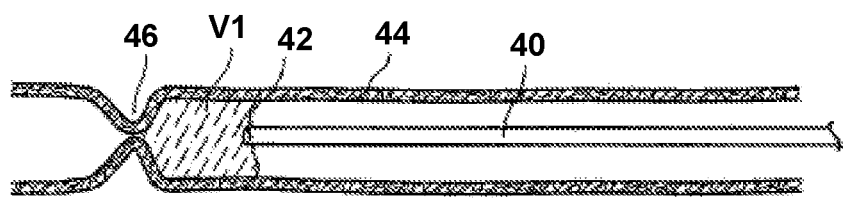

As shown in the example of FIGS. 2A-2E, a flexible catheter 40 may be percutaneously introduced into the vein 44 at an access site and translumenally distally advanced across a treatment zone within the vein 44. External compression, such as manual compression, is applied to collapse the vein 44 distally of the flexible catheter 40 and create a first occlusion 46 as shown in the example of FIG. 2A. After the creation of the occlusion 46 in the vein 44, a first volume V1 within vein 44 can be defined between a distal end 42 of the flexible catheter 40 and the occlusion 46, as illustrated in FIG. 2B. In other examples, external compression may not be needed when the adhesive may be an embolic that occludes blood flow within the vessel.

Figure 2C:
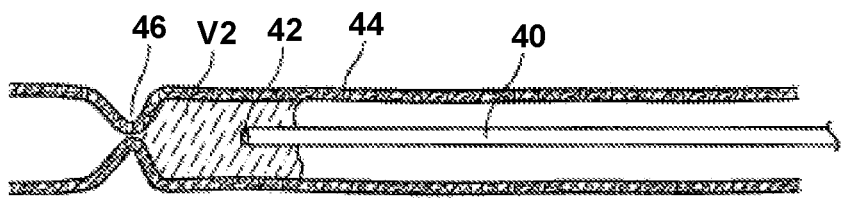
Figure 2D:
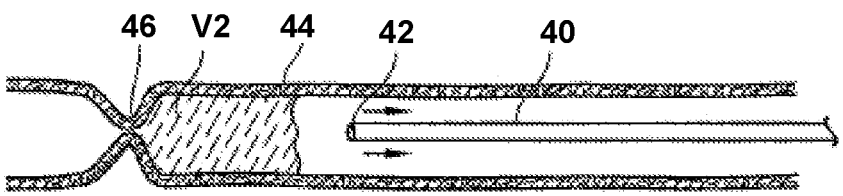
Figure 2E:
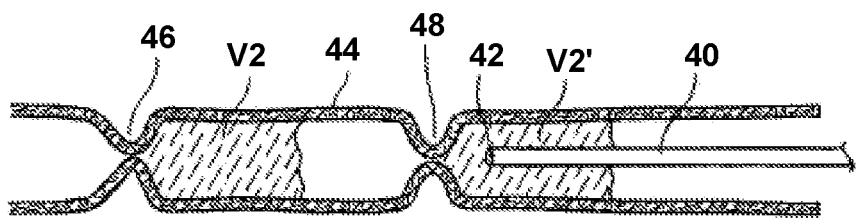

Medical adhesive having a second volume V2, such as in a bolus, can then be injected from the distal end 42 of the flexible catheter 40 into the vein 44 (e.g., by advancing a shaft 18 through the flexible catheter 40 to deliver medical adhesive from the distal end 42 of the flexible catheter 40. In some examples, the second volume V2 (of the medical adhesive injected) is at least about 100%, 105%, 110%, 120%, 125%, 130%, 140%, 150%, 175%, 200%, 250%, or more of the first volume V1 (of the vein 44 in between the occlusion and the distal end 42 of the catheter 40), such that a proximally advancing edge, or meniscus, of media V2 passes proximally past the distal end 42 of the flexible catheter 40, as illustrated in FIG. 2C. The flexible catheter 40 is then withdrawn proximally, as illustrated in FIG. 2D, and a second more proximal occlusion 48 can be created, such as via external compression. Additional medical adhesive can then be injected to create a volume VT greater than the volume within the vein 44 between the distal end 42 of the flexible catheter 40 and the occlusion 48, as illustrated in FIG. 21E. This process can then be repeated for a total of at least 2, 3, 4, 5, 6, 7, 8, 9, 10, or more occlusions depending on the desired clinical result.

Figure 3:
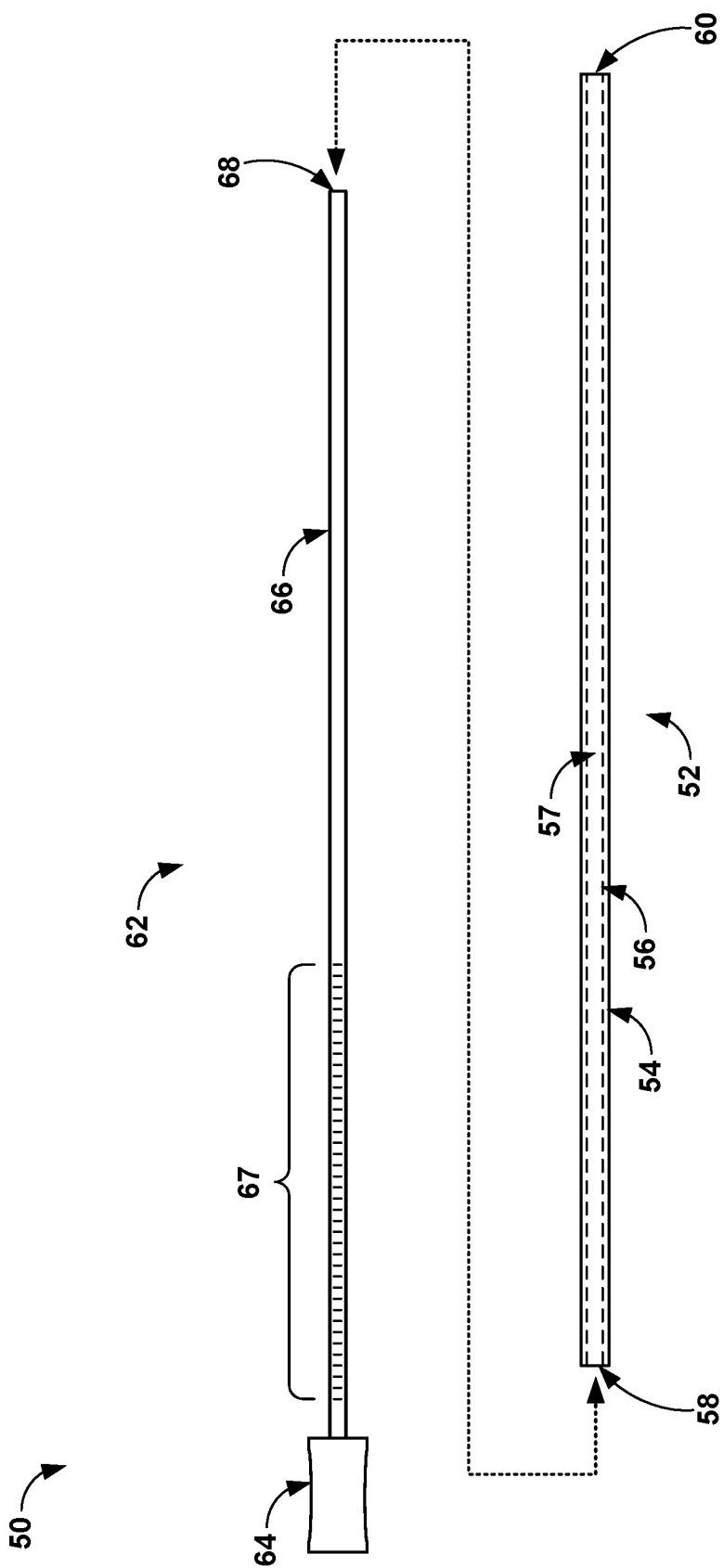
FIG. 3 is a conceptual view of an example catheter and mandrel configured to deliver a vein-occluding substance to a patient

FIG. 3 is a conceptual view of an example system 50 configured to deliver a vein-occluding substance, such as a medical adhesive, to a patient. As shown in FIG. 3, a system 50 includes a flexible catheter 52 and a mandrel 62. The flexible catheter 52 may be similar to the flexible catheter 12 discussed above, and the mandrel 62 may be similar to the shaft 18 discussed above. The flexible catheter 52 may have an exterior wall 54 and an interior wall 56. The interior wall 56 defines a lumen 57, within which medical adhesive or a pre-filled cartridge containing the medical adhesive may be disposed. The flexible catheter 52 may also define a proximal opening 58 to the lumen 57, into which a body 66 of the mandrel 62 may be inserted. Advancement of the body 66 through the lumen 57 may cause medical adhesive or other fluid within the lumen 57 to be dispensed out of a distal end 60 defined by the flexible catheter 12, which corresponds to a distal opening of the lumen 57 in the example shown in FIG. 3.

The mandrel 62 may include a body 66 attached to a handle 64. The mandrel body 66 may be axially stiff and laterally flexible in order to be inserted through the lumen 57 of the flexible catheter 52 and providing a pushing force against adhesive or other medical fluid within the lumen 57. A distal end 68 of the body 66 may have a distal surface (e.g., a flat surface) that is configured to apply a pressure to the medical adhesive within the lumen 57 of the flexible catheter 52. In some examples, the distal surface of the distal end 68 may be rounded, domed, or have a slightly tapered tip that facilitates insertion of distal end 68 into the proximal opening 58 of the flexible catheter 52.

In some examples, the mandrel body 66 includes markings 67 along the axial length of the mandrel body 66. Markings 67 may indicate the amount of medical adhesive delivered from the flexible catheter 52 when comparing the position of the markings with respect to the proximal opening 58. The mandrel body 66 may be constructed of a length that enables the distal end 68 to reach the distal opening 60 of the flexible catheter 52 while the handle 64 is proximal to the proximal opening 58. In other examples, the mandrel body 66 may be constructed of a length that is less than the total length of the flexible catheter 52 in order to maintain a predetermined length of the flexible catheter 52 distal to the mandrel body 66 and flexible end that provides a more atraumatic tip than the distal end 68 of the mandrel body 66.

The handle 64 may be sized for a human hand and promote manipulation of the mandrel body 66. The handle 64 may be constructed of any suitable material, such as, but not limited to, a metal, metal alloy, polymer, or composite material. In some examples, a proximal end of the flexible catheter 52 may include a texturized outer surface or different material that facilitates a user's hand grabbing onto the proximal end of the flexible catheter 52. In some examples, the proximal end of the flexible catheter 52 may have a larger diameter and/or stiffer material that can be manipulated by the user without collapsing the lumen 57. In some examples, the distal end of the mandrel body 66 may be pre-inserted into the proximal opening 58 of the flexible catheter 52 to seal the medical adhesive from the external environment, e.g., during storage of the system 50. In this manner, the manufacturer may deliver a system that includes the mandrel 62 and the flexible catheter 52 pre-filled with a predetermined volume of medical adhesive while maintaining the integrity of the prefilled medical adhesive. An example proximal end of a flexible catheter is shown in FIGS. 4A and 4B.

In other examples, the mandrel body 66 may have a diameter that is the same or larger than the inner diameter of the flexible catheter 52. However, in response to insertion of the mandrel body 66 into the lumen 57, the flexible catheter 52 may expand, or stretch, radially to increase the inner diameter of the flexible catheter 52 to a size that accepts body 66. In this manner, the stretching of the flexible catheter 52 may provide a tight seal around mandrel 66. In addition, or alternatively, the mandrel body 66 may be covered by, or attached to, a compressible tip or non-compressible tip that has a larger diameter than the body 66. In this manner, both the compressible tip and non-compressible tip may contact the inner wall 56 to prevent the adhesive from moving proximally, similar to a plunger of a syringe. The compressible tip may be reduced in diameter when inserted into the lumen 57. The non-compressible tip may be sized just smaller than the lumen diameter in order to slide within the lumen 57 while also preventing most or all of the adhesive from moving proximally past the non-compressible tip.

Figure 4A:
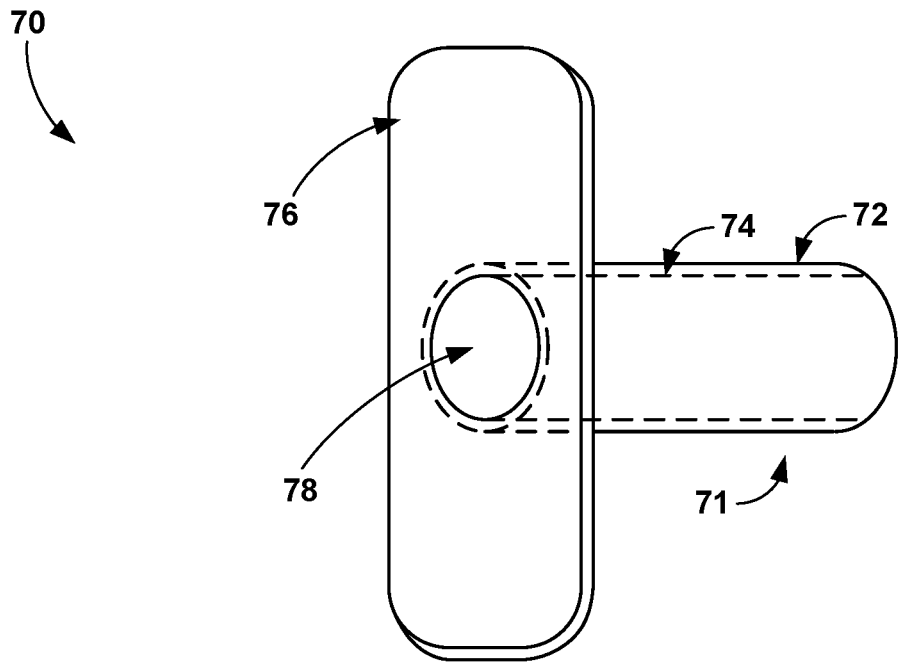
FIGS. 4A and 4B are perspective and cross-sectional views, respectively, of a proximal end of a catheter configured to deliver a vein-occluding substance to a patient.
Figure 4B:
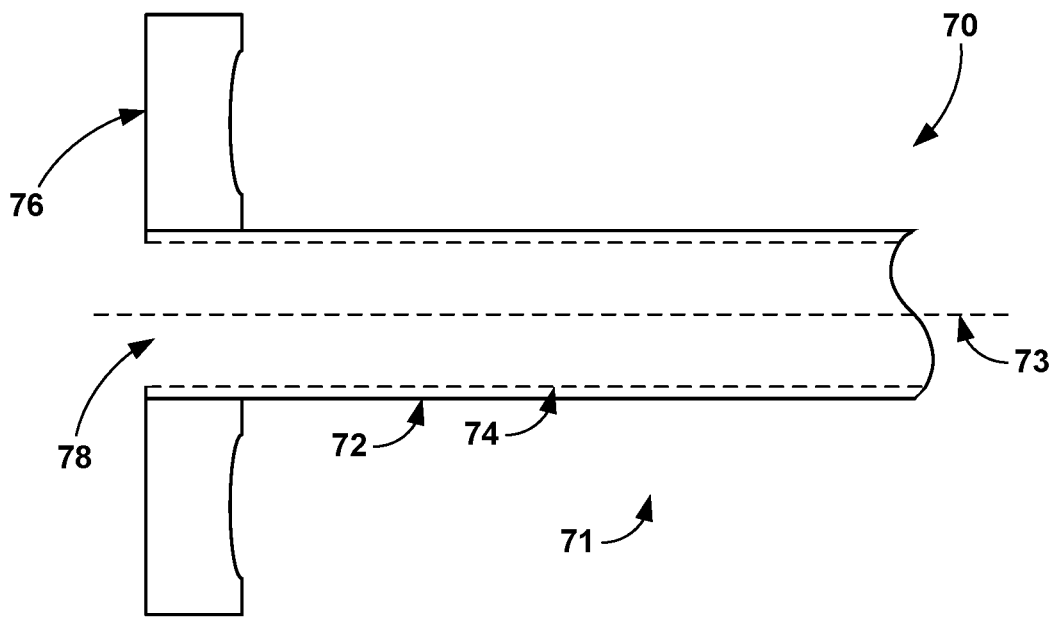

FIGS. 4A and 4B are perspective and cross-sectional views, respectively, of a proximal end of a flexible catheter 70 configured to deliver a vein-occluding substance to a patient. The flexible catheter 70 may be similar to the flexible catheters 12 and 52 discussed herein. As shown in FIG. 4A, the flexible catheter 70 includes an elongated member 71 that defines an external wall 72 and an internal wall 74. The internal wall 74 defines a lumen 78, which is configured to be pre-filled with medical adhesive (or other medical fluid) or accept a pre-filled cartridge containing medical adhesive. A flange 76 is attached to the elongated member 71 and provides a surface a user may hold in order to manipulate the position of the flexible catheter 70, e.g., in order to advance the flexible catheter 70 proximally or distally within vasculature of a patient.

As shown in the cross-sectional view of FIG. 4B, the flange 76 extends transverse to (e.g., perpendicular to) a longitudinal axis 73 of the elongated member 71. The flange 76 may include concave surfaces facing distally to facilitate finger placement from the user when providing a proximal direction force to counteract a distal direction force created by advancing the mandrel 52 through the lumen 78. In other examples, the proximal end of flexible catheter 70 may include a handle around the perimeter of the external wall 72 that enables a user to wrap fingers around the handle and then elongated member 71 when inserting the mandrel 52 into the lumen 78, for example. In any case, the flexible catheter 70 may include a structure on its distal end that facilitates user handling of the flexible catheter 70 and the insertion and advancement of the mandrel 52 or other device such as the shaft 18 (FIGS. 1A-1E).

FIG. 5A is a cross-sectional view of the distal end of an example flexible catheter 80 pre-filled with a vein-occluding substance, such as a medical adhesive, and a shaft 96 within a lumen defined by the flexible catheter 80. The flexible catheter 80 may be an example of the flexible catheters 12, 52, or 70 described herein. The flexible catheter 80 and the shaft 96 may provide a system that facilitates delivery of a medical adhesive into a patient for various treatments, such as the delivery of a medical adhesive to a vein for vessel occlusion. Prior to the medical procedure in which medical adhesive 98 is delivered to a patient, the medical adhesive 98 can be stored within the flexible catheter 80. For example, a lumen of the flexible catheter 80 may be filled with medical adhesive 98 by the manufacturer and then stored and/or shipped for later use by a clinician. In this manner, the flexible catheter 80 may be both the storage and the delivery vessel of the medical adhesive 98. Pre-filling the flexible catheter 80 with a volume of medical adhesive 98 may reduce the overall time for the procedure, reduce the amount of adhesive needed (i.e., the entire length of the catheter does not need to be primed with adhesive), and reduce the likelihood that the single-use flexible catheter 80 can be re-used for a medical procedure performed on another patient.

Pre-filling the flexible catheter 80 with medical adhesive 98 may be in contrast to alternative methods of distributing the medical adhesive which may include a separate vial of medical adhesive that the clinician or other user adds to the flexible catheter 80 prior to use in a procedure, such as by a syringe or other fluid delivery mechanism. In some examples, the flexible catheter 80 may have an increased volume and/or length to store the entire volume of medical adhesive 98 needed to perform a procedure as compared to other catheters that are not pre-filled with a medical adhesive. This may reduce clinician time when preparing for the procedure and reduce the likelihood of medical adhesive reuse for another patient. For example, a pre-filled flexible catheter 80 may eliminate the flexible catheter 80 from needing to be primed, or filled to displace air, by the clinician prior to the procedure.

The example of FIG. 5A shows a distal end 81 of the flexible catheter 80, where the distal end of the shaft 96 has already been inserted within a lumen of the flexible catheter 80. The flexible catheter 80 may be constructed of any suitable material. For example, the flexible catheter 80 may include an outer wall 82 and an inner liner 86. The outer wall 82 may define a cylinder shape and, in some examples, include a reinforced section that includes a reinforcing member 84. The reinforcing member 84 may be a coil, braid, or other structure that provides structural reinforcement to the outer wall 82 that promotes pushability, trackability, and/or rink resistance of the flexible catheter 80. The outer wall 82 may be constructed of one or more polymers (e.g., polytetrafluoroethylene (PTFE) or a thermoplastic such as Pebax®). Since the flexible catheter 80 is prefilled with medical adhesive 98, the flexible catheter 80 may not benefit from being translucent as would otherwise be beneficial during priming of the catheter 80 with medical adhesive. The ability of the flexible catheter 80 to be opaque may enable a broader range of catheter designs, such as a catheter 80 that includes a reinforcing member 84. In addition, in some examples, the outer wall 82 may be filled with an echogenic material, such as ZnO2, TiO2, or the like. (e.g. as described in U.S. Pat. No. 5,921,933 assigned to Medtronic, Inc., incorporated by reference herein). Such an opaque the outer wall 82 may be constructed thinner than those materials that remain translucent. A thinner outer wall 82 may reduce the outer diameter of the flexible catheter 80 which may increase patient comfort and facilitate insertion of the flexible catheter 80. In some examples, the flexible catheter 80 may be constructed with various stiffness profiles. In one example, the proximal end of the flexible catheter 80 may be stiffer than the distal end of the flexible catheter 80. In another example, the distal end of the flexible catheter 80 may be stiffer than the proximal end of the flexible catheter 80.

The reinforcing member 84 may be within the outer wall 82 (e.g., embedded within the outer wall 82 or sandwiched between two layers of outer wall 82, and the reinforcing member 84 may be constructed of a metal, metal alloy, polymer, or composite maters. The reinforcing member 84 may be constructed of a material that is more rigid than the outer wall 82. The inner liner 86 may define the lumen of the flexible catheter 80 for holding medical adhesive 98. The inner liner 86 may be formed or otherwise constructed by a material that is resistant to adhering to medical adhesive 98. For example, the liner 86 may be constructed of PTFE that prevents medical adhesive 98 from adhering to the inner surface of the flexible catheter 80. In addition to, or in an alternative to, the liner 86, the surfaces of the flexible catheter 80 defining the inner lumen in which an adhesive is contained may include a hydrophilic or hydrophobic material selected to resist interaction with the formulation of medical adhesive 98. In some examples, the outer surface of the outer wall 82 may coated with a hydrophilic, hydrophobic, and/or lubricous material to aid in insertion within the vessel of the patient.

The flexible catheter 80 may also include an echogenic portion at the distal portion of the flexible catheter 80, where the echogenic portion promotes visualization under ultrasound imaging. By limiting the echogenic portion to the distal portion of the flexible catheter 80, the rest of the proximal portion of the flexible catheter 80, such as the outer wall 82 and the liner 86, may be thinner to promote a greater volume capacity to hold medical adhesive 98 while enabling a larger inner diameter (lumen) for a given outer diameter of the flexible catheter 80. In this manner, the inner diameter of the flexible catheter 80 may be smaller at the distal end than at more proximal locations in order to accommodate these echogenic materials.

In some examples, echogenic properties of the flexible catheter 80 may be provided by the air channels 92A and 92B disposed at the distal end of the flexible catheter 80 and within wall material 88 (which may be similar to the outer wall 82). The liner 86 may extend to the distal end 81 of the flexible catheter 80 and until the distal opening 94. In some examples, the distal opening 94 may be covered with a flap or breakable cover that is forced open from increased pressure from the shaft 96 against the adhesive 98. In other examples, cap may cover the flexible catheter 80 that is pre-filled with the adhesive 98, and the clinician or other user may remove the cap just prior to insertion of the flexible catheter 80 into the patient. Instead of, or in addition to, the air channels 92A and 92B, the flexible catheter 80 may include other echogenic materials near the distal opening 94. In some examples, a radiopaque marker, such as a metal band 90, positioned at or near the distal end 81 of the flexible catheter 80 to promote visualization under ultrasound, x-ray, fluoroscopy, or other imaging modality. In some examples, the metal band 90 may be coated by a polymer, such as PTFE, the metal band 90 may be disposed on the radially outward surface of the flexible catheter 80, and/or the metal band 90 may be swaged to the distal end of the flexible catheter 80.

The cross-sectional dimension of the shaft 96 (e.g., the diameter or cross-sectional area) is sized to correspond with the cross-sectional dimension of the lumen defined by the liner 86. Therefore, the shaft 96 may have a dimension slightly smaller than that of the liner 86 to enable the shaft 96 to be advanced through the lumen defined by the liner 86 while preventing or reducing any medical adhesive 98 from passing back between the shaft 96 and the liner 86. The shaft 96 may be manually advanced by the user from the proximal end of the flexible catheter 80 (not shown in FIG. 5A). In some examples, the shaft 96 may be delivered out of a coiled carrier tube proximal to the proximal opening of the flexible catheter 80. Since the shaft 96 may be coiled until inserted into the lumen of the flexible catheter 80, a long length of the shaft 96 extending back from the flexible catheter 80 may not complicate maneuvering the flexible catheter 80 or otherwise require additional space near the patient. The shaft 96 may be an example of body 66 of the mandrel 62 described with respect to FIG. 3.

Delivering medical adhesive 98 that was pre-filled within the lumen (filled by medical adhesive 98 and shaft 96 in the example of FIG. 5A) of the flexible catheter 80 may provide advantages over systems in which the medical adhesive is delivered from an injector or syringe that is attached to a proximal end of a catheter. For example, the pre-filled flexible catheter 80 may reduce setup time prior to delivering medical adhesive 98 into a patient, such as time required to prime a syringe and catheter with medical adhesive stored in a vial. In addition, delivery of the medical adhesive 98 from the flexible catheter 80 via force provided from the shaft 96 may reduce the force required to deliver medical adhesive 98 out of the distal opening 94.

As an example, a 3 cubic centimeter (cc) syringe filled with medical adhesive may have a diameter of 0.38 in (0.97 cm). However, the diameter of the lumen within the flexible catheter 80 may be significantly smaller, which reduces the force needed to displace medical adhesive 98 from the flexible catheter 80. This reduction in force may improve deliverability by the user.

Examples of pressure reduction for various different dimensions of the flexible catheter 80 as compared to a 3 cc syringe with a diameter of 0.38 in are described below in Table 1.

TABLE 1

| Example | Vol (cm³) | ID (in) | OD (in) | OD (F) | Wall (in) | Length (cm) | Pressure reduction |
|---|---|---|---|---|---|---|---|
| A | 1.3 | 0.052 | 0.085 | 6.5 | 0.0165 | 91 | 50× |
| B | 2 | 0.075 | 0.085 | 6.5 | 0.005 | 70 | 25× |
| C | 3 | 0.075 | 0.085 | 6.5 | 0.005 | 105 | 25× |
| D | 1.4 | 0.056 | 0.066 | 5 | 0.005 | 91 | 46× |
| E | 2 | 0.056 | 0.066 | 5 | 0.005 | 126 | 46× |

As shown in Table 1, "Vol" is the volume of the flexible catheter 80, "ID" is the inner diameter of the catheter 80 that defines the lumen, "OD" is the outside diameter of the catheter 80, "Wall" is the wall thickness from the lumen to the outer surface of the catheter 80, "Length" is the overall length of the flexible catheter 80 from its proximal end to its distal end, and "Pressure Reduction" is the estimated pressure reduction as compared to a system that delivers medical adhesive using a 3 cc syringe attached to a catheter with dimensions of the catheter of example A.

Table 1 indicates that reductions to the inner diameter, and, thus, the cross-sectional area, of the lumen of the flexible catheter 80 generally reduces the pressure as compared to the syringe. In order to increase the volume of the flexible catheter 80 while also maintaining reduced delivery pressures, a longer length of the flexible catheter 80 may be used. These dimensions of the flexible catheter 80 may be adjusted for certain use cases. For example, the length of the flexible catheter 80, inner diameter, and/or outer diameter may be reduced to hold less volume of medical adhesive 98 when a smaller vessel (e.g., perforator vein or spider vein) is to be treated. In these examples, smaller shafts may be used to correspond with smaller inner diameter flexible catheters such as the flexible catheter 80.

In addition to decreasing required pressures for delivery as compared to using a syringe, delivering medical adhesive 98 by advancing a shaft 96 through a catheter lumen may reduce compliance in the adhesive delivery system and enable a more controlled delivery of medical adhesive 98. This reduced compliance may also reduce the amount of "dribble" of medical adhesive that continues to flow from distal opening 94 after the user stops applying pressure to shaft 96. However, the flexible catheter 80 may be constructed to provide a desired amount of dribble that the clinician may be expecting to finish delivery of a bolus of the medical adhesive 98.

In some examples, the shaft 96 and/or a handle portion attached to a proximal portion of shaft 96 may include indents or detents that interface with the flexible catheter 80 to provide tactile feedback to the user on the delivery amount of medical adhesive from distal opening 94. In addition, or alternatively, the shaft 96 can include visual markers on a proximal portion that becomes covered by the flexible catheter 80 as the shaft 96 is advanced distally into the catheter lumen to indicate how much volume of medical adhesive 98 was delivered out of distal opening 94 as the distance shaft 96 was advanced distally with respect to the flexible catheter 80. For example, the visual markers of the shaft 96 may be substantially similar to the markers 67 of the body 66 of the mandrel 62 of illustrated in FIG. 3.

FIGS. 5B and 5C are cross-sectional views of different axial positions A and B, respectively, along the catheter of FIG. 5A. As shown in FIG. 5B, the liner 86 of the catheter 80 is radially inward of the outer wall 82. The liner 86 may define the catheter lumen configured to receive the shaft 96. As shown in FIG. 5C, the distal end of the flexible catheter 80 includes metal band 90 defining an outside surface around a wall 88. The wall 88 may be constructed of the same or similar material as the outer wall 82. The liner 86 is disposed radially within the wall 88 and defines the lumen within which the medical adhesive 98 is disposed. The wall 88 also defines two air channels 92A and 92B, which provide the catheter 80 with echogenic features. In other examples, a single air channel or three or more air channels may be defined by wall 88.

As shown in FIGS. 5A and 5C, the diameter of the catheter lumen within axial position B is smaller than axial position A of the flexible catheter 100. This smaller lumen diameter may result from the addition of echogenic materials (e.g., air channels 92A and 92B) and/or the metal band 90 as compared to proximal portions of the flexible catheter 80. The smaller diameter at the axial position B may also be smaller than the diameter of the shaft 96 to help keep the shaft 96 within catheter 80 during a medical procedure and prevent the shaft 96 from exiting the distal opening 94 and adversely impacting tissue of the patient.

FIG. 6A is a cross-sectional view of the distal end of an example flexible catheter 100 pre-filled with medical adhesive 98 and defining a guidewire the exit port 116. FIG. 6A also illustrates a shaft 120 inside an inner lumen 114 of the catheter 100. As shown in the example of FIG. 6A, the flexible catheter 100 includes the outer wall 102, a reinforcing member 104, and an inner liner 106. The flexible catheter 100 and the shaft 120 may be substantially similar to the flexible catheter 80 and the shaft 96, respectively, of FIG. 5A. For example, the outer wall 102 of the catheter 100 may be similar to the outer wall 82, the reinforcing member 104 may be similar to the reinforcing member 84, the inner liner 106 may be similar to the inner liner 86, and the shaft 120 may be similar to the shaft 96. However, the flexible catheter 100 defines a guidewire exit port 116 configured to receive a guidewire 118 that may be used to facilitate navigation of the flexible catheter 100 to a target site within a vessel (or other hollow anatomical structure) of the patient. The shaft 120 is configured to be disposed within the lumen 114 defined by the liner 106 and proximal to the medical adhesive 98 contained within the lumen 114.

The outer wall 102 defines an exit port 116, which is an opening from the lumen 114 to the outside of the flexible catheter 100. One end of a flap 108 is attached to the outer wall 102 and the remainder of the flap 108 is dimensioned to extend across the lumen 114 to block flow through the lumen 114 past the flap 108. For example, the remainder of the flap 108 may be sized and configured to match the cross-sectional area of lumen 114 and seal medical adhesive 98 proximal to the flap 108 and the exit port 116. In this manner, the flexible catheter 100 can be pre-filled with medical adhesive 98 while also enabling the use of the guidewire 118. The guidewire 118 may be navigated to a target treatment site within the vessel, and then the flexible catheter 100 may be navigated to the target treatment site inserted over the guidewire 118. In this manner, the guidewire 118 may extend through the exit port 116 and out of the distal opening 122. The flexible catheter 100 may thus be referred to as a rapid exchange catheter in some examples.

The flap 108 may be constructed as one or more layers of material (e.g., a polymer such as polyurethane, a metal or metal alloy, or composite material) that form a movable membrane. In some examples, the flap 108 may be constructed of collagen or some other biological based material configured to occlude the exit port 116, and when the flap 108 is "opened" to open the lumen 114 and enable flow of fluid through the lumen 114 and distal to the exit port 116. The flap 108 may be configured to stay in place to hold medical adhesive 98 proximal to the exit port 116 until a sufficient force is applied to the flap 108 from the medical adhesive 98. When the guidewire 118 is removed from the flexible catheter 100, advancement of the shaft 120 may increase the pressure applied to medical adhesive 98 until the pressure forces the distal movement of medical adhesive 98 to cause the flap 108 to move distally to cover the exit port 116 (as shown in FIG. 7A).

Once the flap 108 covers the exit port 116, medical adhesive 98 may flow towards the distal opening 122 without medical adhesive exiting through the exit port 116. In some examples, the flap 108 may be glued to an inner surface of the outer wall 102 and/or the liner 106. For example, a proximal portion 110 of the flap 108 may be adhered to the inner or exterior surface of the outer wall 102. In other examples, the proximal portion 110 of the flap 108 may be formed from or otherwise attached to the outer wall 102 and/or the liner 106. A distal portion 112 of the flap 108 may also be adhered to the liner 106, friction fit in place, or otherwise set against liner 106 to seal medical adhesive 98 within the lumen 114 proximal to the flap 108. However, in some examples, the distal portion 112 may refer to the outer edges of the flap 108 when the flap 108 is circular in shape. In any case, the distal portion 112 may be less strongly adhered or attached to the flexible catheter 100 such that the pressure from medical adhesive 98 causes the distal portion 112 to release while the proximal portion 110 remains attached to prevent the flap 108 from being detached. In other examples, the flap 108 may define a perforated, thinned, or pre-slit portion that breaks in response to higher pressures from medical adhesive 98. The remnants of the flap 108 may still be sized to fold over against the inner wall of the liner 106 and cover the exit port 116.

The exit port 116 may be a side opening defined by the outer wall 116 and the liner 106. The exit port 116 may be disposed distal to the medical adhesive 98 pre-filled within the lumen 114 of the flexible catheter 100. The exit port 116 may be sized to accept one or more different dimensioned guidewires 118. The exit port 116 may be defined by surfaces perpendicular with the longitudinal axis of the flexible catheter 100 such that a longitudinal axis defined by the exit port 116 is perpendicular to the longitudinal axis of the flexible catheter 100. In other examples, the exit port 116 may be defined by an oblique surface within the outer wall 102 and/or the liner 106 such that the longitudinal axis of the exit port 116 is not parallel or perpendicular to the longitudinal axis of the flexible catheter 100. The oblique surface may help guide the guidewire 118 into the lumen 114 distal to the adhesive 98.

FIGS. 6B and 6C are cross-sectional views of different axial positions C and D, respectively, along the flexible catheter 100 of FIG. 6A. As shown in FIG. 6B, the flexible catheter 100 includes the inner liner 106 radially inward of the outer wall 102. The liner 106 may define the lumen 114, within which the shaft 120 is disposed. As shown in FIG. 6C, the distal end of the flexible catheter 100 includes the outer wall 102 radially outward of the liner 106. The liner 106 defines lumen 114, and the guidewire 118 is disposed within lumen 114.

FIGS. 7A and 7B are cross-sectional views parallel with the longitudinal axis of the flexible catheter 100 from FIG. 6A in which the guidewire 118 is removed from the exit port 116. In the example of FIG. 6A, the flap 108 is in a first position that blocks the lumen 114 and retains the volume of medical adhesive 98 proximal to the flap 108 and the exit port 116. However, as shown in FIG. 7A, the flap 108 is configured to move from the first position to a second position, in which the flap 108 closes the exit port 116 (e.g., a side opening in the flexible catheter 100) from lumen 114.

Once the flexible catheter 100 is positioned at the target location within the patient, a clinician may proximally withdraw the guidewire 118 from the lumen 114 via the exit port 116. At this point, the flap 108 may remain in the first position to hold medical adhesive 98 proximal to the exit port 116. When the clinician desires to deliver medical adhesive 98 from the distal opening in the flexible catheter 100, the clinician may advance the shaft 120 in the distal direction (as indicated by arrow 124), which increases the pressure of the medical adhesive 98 and advances medical adhesive 98 distally within the lumen 114 to force the flap 108 from the first position to the second position. The proximal portion 110 of the flap 108 may act like a hinge to enable the rest of the flap 108 to move within lumen 114.

The second position of the flap 108 is shown in FIG. 7A, where the distal portion 112 of the flap 108 contacts a portion of the liner 106 and/or the outer wall 102 distal to the exit port 116 in order to close off the lumen 114 from the exit port 116. In the second position, the flap 108 enables the medical adhesive 98 to flow along a radially inward facing surface of the flap 108 and into the distal portion of the lumen 114 until at least a portion of medical adhesive 98 exits the flexible catheter 100 through the distal opening.

In some examples, some or all of the flap 108 may be configured to contact the inward facing portions of the outer wall 102 at a region in which liner 106 is not disposed. In this manner, the flap 108 may be substantially flush with the liner 106 when in the second position as shown in FIG. 7A. In other examples, the flap 108 may be attached to and/or in contact with liner 106 in the second position. Since the flap 108 may be relatively thin, the resulting reduction in lumen diameter may not significantly affect the advancement of medical adhesive 98 or the shaft 120 within the catheter lumen 114. However, the flap 108 may be constructed of a material that has a stiffness and/or thickness that resists the pressure from medical adhesive 98 generated by the advancement of shaft 100 to prevent medical adhesive 98 from passing out of the exit port 116.

As shown in FIG. 7B, the flap 108 in the second position may enable the distal end of the shaft 120 to pass distally of the flap 108 and the exit port 116. For example, the distal portion 112 of the flap 108 may rest against the liner 106 and/or the outer wall 102 and not inhibit the advancement of the shaft 120. Therefore, the flap 108 may not interfere with the shaft 120 to moving distal to the exit port 112 to continue dispensing medical adhesive 98 from the distal opening of the catheter 100 until the procedure is complete or all of medical adhesive 98 has been delivered from the flexible catheter 100.

FIG. 8A is a cross-sectional view of the distal end of an example flexible catheter 130 configured to accept a pre-filled cartridge 144 filled with a vein-occluding substance such as a medical adhesive 98. The flexible catheter 130 may be an example of flexible catheters 12, 52, or 70 described herein that facilitates delivery of medical adhesive 98 for various treatments, such as the delivery of medical adhesive 98 to a vein for vessel occlusion. In addition, the flexible catheter 130 may be similar to the flexible catheter 80 and be configured to receive a shaft (such as the shaft 152 shown in FIG. 9A) that is similar to the shaft 96. For example, the outer wall 132 may be similar to the outer wall 82, the reinforcing member 134 may be similar to the reinforcing member 84, the inner liner 136 may be similar to the inner liner 86, the outer wall 138 may be similar to the outer wall 88, the metal band 140 may be similar to the metal band 90, and the air lumens 142A and 142B may be similar to the air lumens 92A and 92B. However, the flexible catheter 130 may be configured to receive the pre-filled cartridge 144 which is a structure separate from the catheter 130 and contains a predetermined volume of medical adhesive 98.

The pre-filled cartridge 144 may be a sealed tube or other container defined by at least a side wall 148C, a proximal wall 148A, and a distal wall 148B. The outer diameter (or other cross-sectional dimension) of the pre-filled cartridge 144 may correspond to the cross-sectional dimension of catheter lumen 133 of the catheter 130. In this manner, the outer diameter of the pre-filled cartridge 144 may be smaller than the diameter of the lumen 133 to facilitate insertion of the pre-filled cartridge 144 into the lumen 133. The pre-filled cartridge 144 may be filled with a predetermined volume of medical adhesive 98 by a manufacturer, and the pre-filled cartridge 144 may be stored and delivered to a user for insertion into the flexible catheter 130 prior to performing the procedure on the patient. In this manner, the user may insert the pre-filled cartridge 144 into lumen 133 defined by the liner 136 when the flexible catheter 130 is completely outside of the patient or after the flexible catheter 130 is positioned within the target vessel.

The proximal wall 148A and the distal wall 148B of the pre-filled cartridge 144 may be configured to rupture in response to pressure applied to the walls 148A, 148B either directly or indirectly by a shaft (e.g., the shaft 152 of FIG. 9A). Therefore, advancement of the shaft 152 may cause medical adhesive 98 to flow out of distal opening 150 defined by the distal tube 146 of the pre-filled cartridge 144. Although the distal tube 146 is shown as protruding distally of the distal end of the flexible catheter 130, the distal tube 146 may terminate at the same position or proximally from the distal end of the flexible catheter 130 in other examples.

In other examples, the flexible catheter 130 may be pre-loaded with the pre-filled cartridge 144 by the manufacturer. However, a benefit of the pre-filled cartridge 144 may be that additional pre-filled cartridges may be inserted into the flexible catheter 130 if additional medical adhesive 98 is required during the procedure. A spent (e.g., empty or otherwise used) pre-filled cartridge 144 may be removed from the lumen 133 of the flexible catheter 130 by withdrawing the shaft 152 used to push medical adhesive 98 out of the distal opening 150. For example, the pre-filled cartridge 144 may be friction fit to the shaft 152 or otherwise in contact with the shaft 152 sufficient to be withdrawn proximally out of the proximal end of the flexible catheter 130 in response to proximal withdrawal of the shaft 152 from the catheter lumen 133. Alternatively, the spent pre-filled cartridge 144 may remain within the catheter lumen 133 and the subsequent pre-filled cartridge may "stack" proximally from the cartridge 144 such that the additional medical adhesive flows through the spent cartridge 144 as it is expelled from another pre-filled cartridge and prior to being delivered to the patient. In yet another example, the outer wall 138 at the distal end of the flexible catheter 130 may be removably attached, such as by threading the outer wall 138 to the distal end of the flexible catheter 130. In such an example, the outer wall 138 may be removed from the flexible catheter 130, the spent cartridge 144 removed, a new pre-filled cartridge 144 inserted, and the outer wall 138 re-attached.

The pre-filled cartridge 144, such as the proximal wall 148A, the distal wall 148B, and the side wall 148C, may be formed from any suitable material, such as, but not limited to, a polymer such as polypropylene, high density polyethylene (HDPE), or PTFE. Materials such as these may exhibit a low coefficient of friction and enable insertion of the pre-filled cartridge 144 through the lumen 133 of the flexible catheter 130. In some examples, the pre-filled cartridge 144 may include an echogenic region such that the position of the pre-filled cartridge 144 may be visible under ultrasound imaging.

The proximal wall 148A of the pre-filled cartridge 144 may be configured to be removed, punctured, or ruptured by the shaft 152. In some examples, the distal end of the shaft 152 may be tapered to facilitate puncturing of proximal wall 148A. In some examples, the proximal wall 148A may be configured as a cap that can be removed or punctured prior to or during use. The distal wall 148B of the pre-filled cartridge 144 may also be configured to be removed, punctured, or ruptured by the increased pressure generated in medical adhesive 98 by the distal advancement of the shaft 152 within the catheter lumen 133. In other examples, the distal wall 148B may be a cap or cover that is configured to be removed or punctured prior to the user inserting the pre-filled cartridge 144 within the catheter lumen 133.

In some examples, the outer wall 138 at the distal end of the flexible catheter 130 may have a greater thickness than the outer wall 132, which results the inner lumen 133 having a smaller diameter at the distal portion of the catheter. For example, the outer wall 132 may define a shoulder 141. This shoulder 141 may prevent the pre-filled cartridge 144 from being advanced out the distal end of the flexible catheter 130. Put another way, the shoulder 141 may enable the advancement of the shaft 152 to increase the pressure within the pre-filled cartridge 144 such that medical adhesive 98 can be dispensed out from distal opening 150 without the pre-filled cartridge 144 itself being pushed out the distal end of the catheter 130.

Providing medical adhesive 98 by way of one or more pre-filled cartridges 144 may provide one or more advantages over syringe-based delivery of medical adhesive. For example, the use of pre-filled cartridges may reduce the risk of adhesive and/or device reuse in another patient. Since the pre-filled cartridge 144 has already been within a patient, a clinician may not attempt to deliver any remaining medical adhesive 98 within a different patient. In addition, even if some medical adhesive 98 remains after treating one patient, this relatively small amount of medical adhesive 98 may have little value for use on another patient. Delivery of medical adhesive 98 via pre-filled cartridges such as the pre-filled cartridge 144 may also facilitate adding more medical adhesive for a procedure when needed and reduce possible waste of medical adhesive from a patient that only requires a small volume of medical adhesive. In some examples, pre-filled cartridges may be constructed with different volumes of medical adhesive 98 for certain types of vessels or procedures so that the clinician can use a pre-filled cartridge with the appropriate volume of medical adhesive. For example, the length of the pre-filled cartridge 144 and/or diameter of the pre-filled cartridge 144 may be specified to hold a certain volume of medical adhesive 98.

FIGS. 8B and 8C are cross-sectional views of different axial positions B and C, respectively, along the flexible catheter 130 of FIG. 8A. As shown in FIG. 8B, the inner liner 136 of the catheter 130 is radially inward of the outer wall 132. The liner 136 may define the lumen 133, within which the side wall 148C of the pre-filled cartridge 144 is disposed. In addition, the pre-filled cartridge 144 contains medical adhesive 98. As shown in FIG. 8C, the distal end of the flexible catheter 130 includes a metal band 140 defining an outside surface around the wall 138. The wall 138 may be constructed of the same or similar material as the outer wall 132. The wall 138 also defines two air channels 142A and 142B, which are echogenic features that configure the distal portion of the catheter 130 to be seen by ultrasound imaging. In other examples, a single air channel or three or more air channels may be defined by wall 138. The liner 136 is disposed radially within the wall 138 to define the lumen 133 within which distal tube 146 of the pre-filled cartridge 144 is disposed. Medical adhesive 98 may be dispensed through the distal opening 150 defined by the distal tube 146 of the pre-filled cartridge 144.

FIGS. 9A and 9B are cross-sectional views of example the flexible catheter 130 from FIG. 8A and illustrates a state in which the shaft 152 of a mandrel has been advanced distally through the catheter lumen 133 to force medical adhesive 98 out of the pre-filled cartridge 144. As shown in FIG. 9A, the cross-sectional dimension of the shaft 152 is sized to correspond with, and be disposed within, a cross-sectional dimension of the lumen 133 defined by the inner surface of the cartridge side wall 148C. Therefore, advancement of the distal end of the shaft 152 through a proximal portion of the pre-filled cartridge 144 forces at least a portion of medical adhesive 98 out of a distal end of the pre-filled cartridge 144 and out of the distal opening 150 of the pre-filled cartridge 144 and the distal opening of the flexible catheter 130.

As shown in FIG. 9B, advancement of the shaft 152 in the direction of arrow 154 causes the cartridge proximal wall 148A to break free of its position and be moved with the distal end of the shaft 152 through the lumen of the pre-filled cartridge 144. In other examples, the cartridge proximal wall 148A may be punctured or ruptured such that the proximal wall 148A remains attached to the side wall 148C, but the shaft 152 can pass through the proximal wall 148A and contact the proximal edge of the volume of medical adhesive 98 stored within the pre-filled cartridge 144. The increased pressures within medical adhesive 98 caused by advancement of the shaft 152 may cause the cartridge distal wall 148B to rupture and allow medical adhesive to flow out of the pre-filled cartridge 144, e.g., past the distal wall 148B, through the distal tube 146, and out of the distal opening 150. In other examples, the cartridge distal wall 148B may be removed by the user prior to inserting the pre-filled cartridge 144 within the flexible catheter 130.

In other examples, the shaft 152 may be constructed with a diameter that is larger than the diameter of the lumen of the pre-filled cartridge 144 and smaller than the diameter defined by the catheter inner liner 136. Therefore, advancement of the shaft 152 may collapse the cartridge side wall 148C as medical adhesive 98 is advanced out of the distal opening 150. Additional pre-filled cartridges may still be inserted within the flexible catheter 130 if needed, as pressure from the shaft 152 may still cause the additional medical adhesive from the subsequent pre-filled cartridge(s) to flow past the first the pre-filled cartridge 144 and out of distal opening 150. The collapsed spent cartridge(s) may then remain within the flexible catheter 130 and discarded once the procedure is completed for the patient.

Figure 10A:
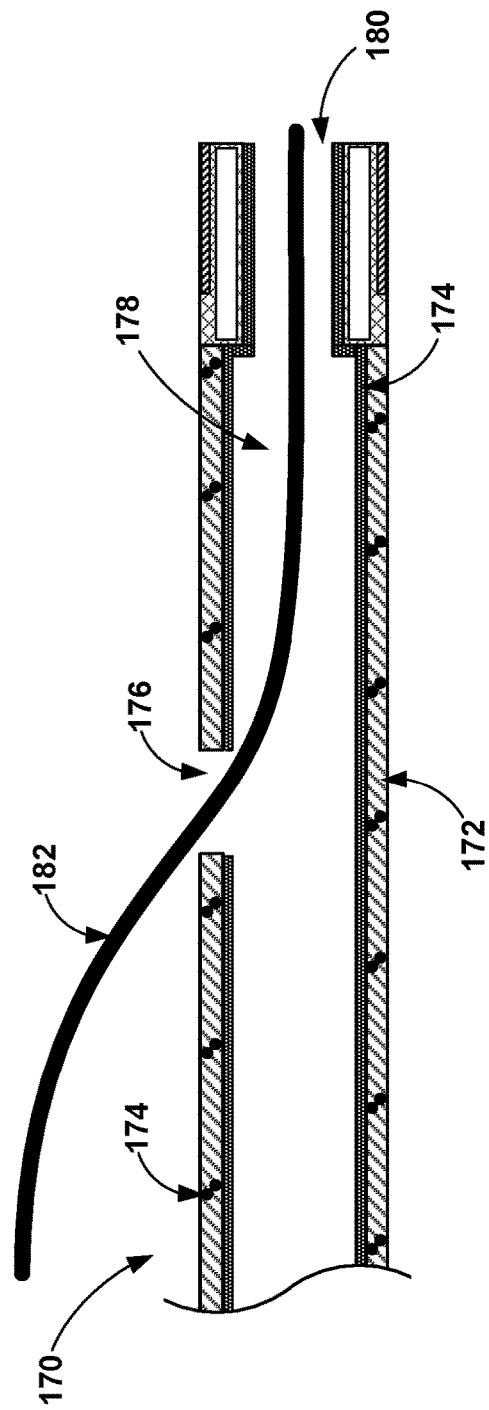
FIGS. 10A and 10B are cross-sectional views of an example catheter and a guidewire exit port that is closed by advancement of a pre-filled cartridge containing a vein-occluding substance.
Figure 10B:
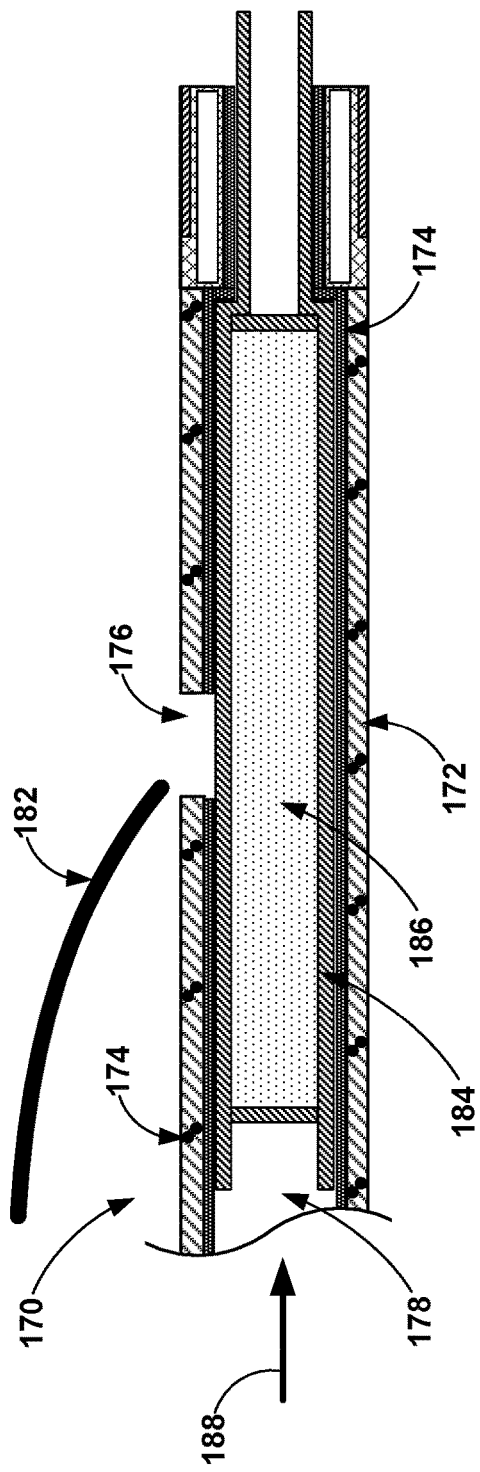

In some examples, a catheter that configured to receive a pre-filled cartridge of a medical adhesive may be a rapid-exchange type catheter. FIGS. 10A and 10B are cross-sectional views of an example of such a catheter 170 and an example guidewire 182 configured to be inserted through a guidewire exit port 176 defined by the catheter 170. As shown in the example of FIG. 10A, the flexible catheter 170 includes an outer wall 172, a reinforcing member 174, and an inner liner 174. The flexible catheter 170 may be substantially similar to the flexible catheter 130 of FIG. 8A. For example, the outer wall 172 may be similar to the outer wall 132, the reinforcing member 174 may be similar to reinforcing member 134, and the liner 174 may be similar to liner 136. The pre-filled cartridge 184 is similar to the pre-filled cartridge 144 and contains a volume of medical adhesive 186 that is similar to the medical adhesive 98. However, the flexible catheter 170 may define the guidewire exit port 176 to facilitate navigation of the flexible catheter 170 through vasculature of a patient to a desired location within a vessel of the patient.

The outer wall 172 defines the exit port 176, which is an opening from the catheter lumen 178 to the outside of the flexible catheter 170. The exit port 176 may be a side opening defined by at the outer wall 172 and the inner liner 174. The exit port 176 may be sized to accept one or more different dimensioned guidewires 182. The exit port 176 may be defined by surfaces perpendicular with the longitudinal axis of flexible catheter 170 such that a longitudinal axis defined by the exit port 176 is perpendicular to the longitudinal axis of the flexible catheter 170. In other examples, the exit port 176 may be defined by oblique surface within the outer wall 172 and/or the liner 174 such that the longitudinal axis of the exit port 176 is not parallel or perpendicular to the longitudinal axis of the flexible catheter 170.

The guidewire 182 may be navigated to a target location within the vasculature of the patient, and then the flexible catheter 170 may be navigated to the target location over the guidewire 182. In this manner, the guidewire 182 may extend through the exit port 176 and out of the distal opening 180. The flexible catheter 170 may thus be referred to as a rapid exchange catheter in some examples.

In the example of FIG. 10A, the pre-filled cartridge 184 has not yet been inserted within the catheter lumen 178 or has been inserted but remains proximal to the exit port 176. When the guidewire 182 is removed from the flexible catheter 170, as shown in FIG. 10B, distal advancement of the pre-filled cartridge 184 in the direction of the arrow 188 may position the pre-filled cartridge 184 adjacent to the exit port 176. In this manner, a portion of the pre-filled cartridge 184 covers and closes the exit port 176 to prevent medical adhesive 186 from being expelled through the exit port 176 in response to advancement of the shaft 152 against the pre-filled cartridge 184.

In some examples, the flexible catheter 170 may include a flap similar to the flap 108 of the flexible catheter 100 in FIG. 6A. The flap may be configured to move between a first position that enables the guidewire 182 to enter the exit port 176 and a second position that closes the exit port 176 from the lumen 178. Distal advancement of the pre-filled cartridge 184 in the direction of the arrow 188 within the catheter lumen 178 may force the flap from the first position to the second position that closes the exit port 176 to help prevent medical adhesive 186 from being expelled out the exit port 176. The pre-filled cartridge 184 may then slide past the flap and hold the flap in the second position against the exit port 176.

Figure 11:
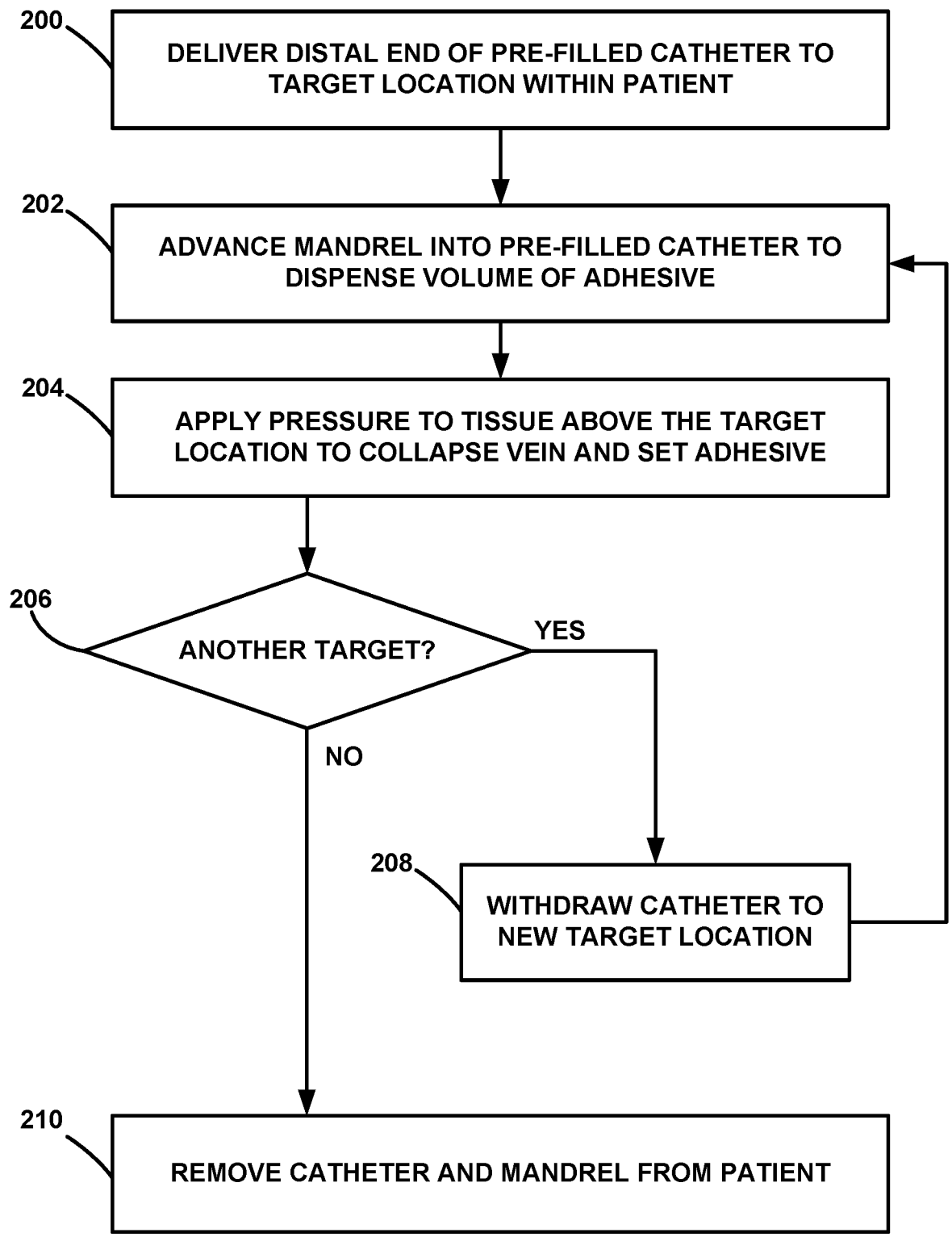
FIG. 11 is a flow diagram of an example technique for delivering a volume of vein-occluding substance out of a catheter pre-filled with the vein-occluding substance by advancing a mandrel within the catheter.

FIG. 11 is a flow diagram of an example technique for delivering a volume of vein-occluding substance, such as a medical adhesive, out of a catheter pre-filled with the vein-occluding substance by advancing a shaft within the catheter. For illustrative purposes, the techniques of FIG. 11 are described with reference to the various aspects of the flexible catheter 80 and shaft 96 of FIG. 5A. However, such descriptions are not intended to be limiting and the techniques of FIG. 11 may be used with other devices or systems, such as flexible catheters 12, 40, 54, 100, shafts 18 or 120, and/or the mandrel 62.

As shown in the example of FIG. 11, a user may insert or deliver a distal end of the flexible catheter 80 to a target location within a hollow anatomical structure of a patient, such as a vein (200). In some examples, a user may use an ultrasound transducer to visualize the target location and the distal end of the flexible catheter 80. The flexible catheter 80 may be pre-filled with medical adhesive 98 to be delivered to the patient. In some examples, the user may insert the flexible catheter 80 without the aid of other devices. For example, the catheter 80 may include the reinforcing member 84 or other structural features that increase the structural integrity and pushability of the catheter 80 to enable the catheter 80 to be navigated through the vasculature without the aid of a guide device (e.g., a guidewire or a guide catheter). In other examples, the user may use a guide catheter within which the flexible catheter 80 may be inserted to the target location. Alternatively, or additionally, the user may use a guidewire (e.g., the guidewire 118) to navigate the flexible catheter 100 to a target location within the patient and remove the guidewire from the catheter 100 prior to delivering the medical adhesive 98.

Once the flexible catheter 80 is positioned at the target location, the user may advance shaft 96 through at least a portion of the lumen of the flexible catheter 80 to force at least a first portion of the volume of medical adhesive 98 (e.g., a bolus) out of distal opening 94 of the lumen of the flexible catheter 80 (202). The user may then apply pressure to the tissue above the target location that received the first portion of medical adhesive to collapse the vein and set the medical adhesive (204). If there is another target location within then vein ("YES" branch of block 206), then the user may proximally withdraw the flexible catheter 80 and position the distal end of the flexible catheter 80 at the new target location (208). The user may then advance shaft 96 further through the lumen of the flexible catheter 80 in order to deliver a second portion of the volume of medical adhesive 98 to the section target location of the vessel (202). This process may be repeated until the entire length of the vessel has been coapted with medical adhesive 98. If there is no other target area to be treated by medical adhesive 98 ("NO" branch of block 206), then the user may remove the flexible catheter 80 and shaft 96 (e.g., part of the mandrel) from the patient (210).

In some examples, the volume of medical adhesive 98 delivered from the flexible catheter 80 may be within a range from approximately 1.0 mL to approximately 4.0 mL. This volume may be different for the treatment of different vessels. For example, treatment of the greater saphenous vein may require a larger volume of medical adhesive than treatment of a perforator vein. Therefore, different flexible catheters may be pre-filled with different volumes of medical adhesive such that some pre-filled flexible catheters may be specified for treatment of certain vessels. These different available volumes may reduce medical adhesive waste for smaller vessels or smaller treatment areas.

Figure 12:
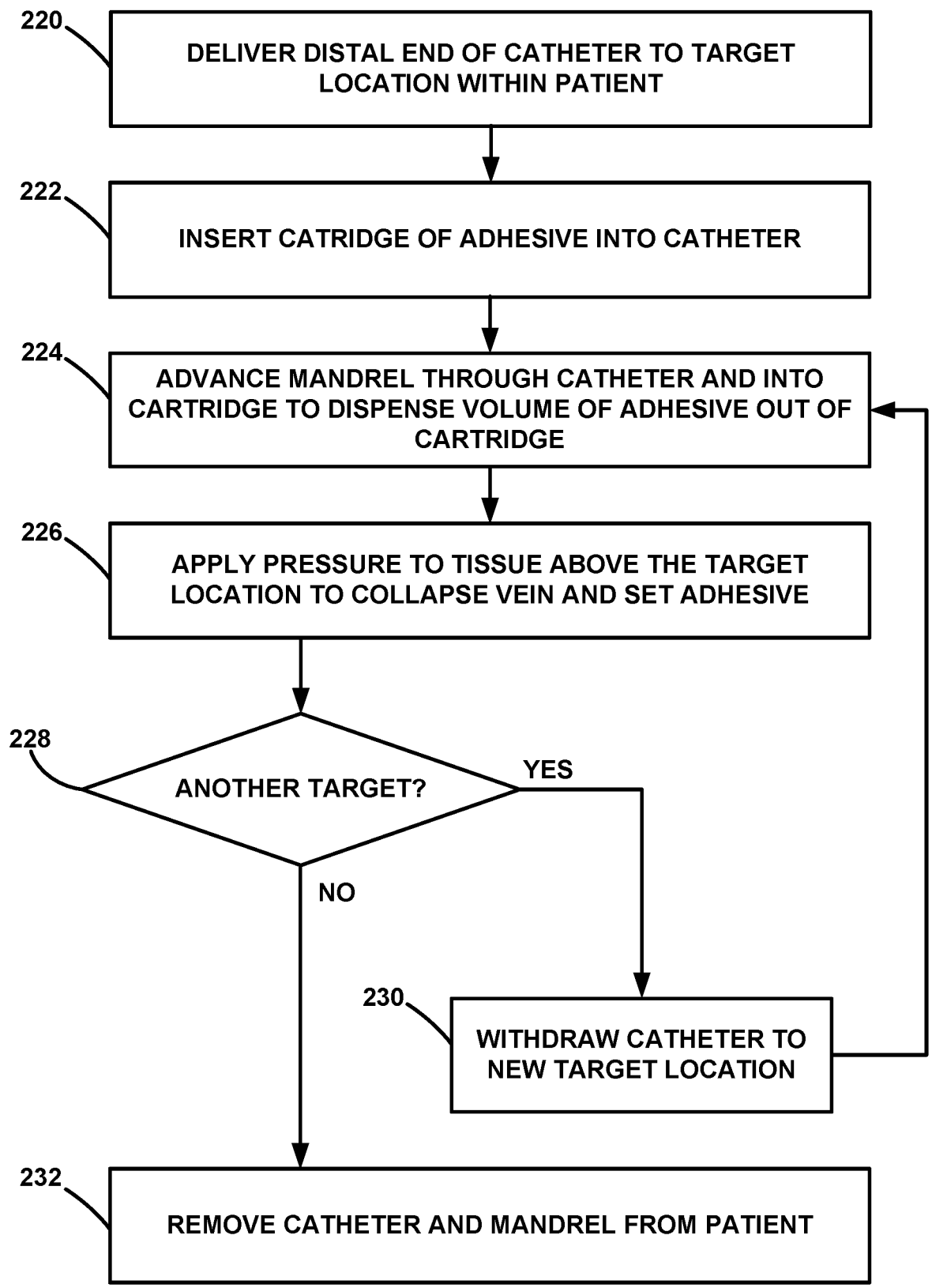
FIG. 12 is a flow diagram of an example technique for inserting a pre-filled cartridge containing a vein-occluding substance and advancing a mandrel to deliver a volume of vein-occluding substance out of the pre-filled cartridge and the catheter.

FIG. 12 is a flow diagram of an example technique for inserting a pre-filled cartridge containing a vein-occluding substance in a catheter lumen and advancing a shaft through the catheter lumen to deliver a volume of vein-occluding substance out of the pre-filled cartridge and the catheter. For illustrative purposes, the techniques of FIG. 12 are described with reference to the various aspects of the flexible catheter 130 and the shaft 152 of FIGS. 8A, 9A, and 9B. However, such descriptions are not intended to be limiting and the techniques of FIG. 12 may be used with other devices or systems, such as flexible catheters 12, 40, 54, 170, the shaft 18, and/or the mandrel 62.

As shown in the example of FIG. 12, a user may insert or deliver a distal end of the flexible catheter 130 to a target location within a hollow anatomical structure of a patient, such as a vein (220). In some examples, a user may use an ultrasound transducer to visualize the target location and distal end of the flexible catheter 130. In some examples, the user may insert the flexible catheter 130 without the aid of other devices. For example, reinforcing member 134 or other structural features of the flexible catheter 130 may increase the structural integrity and pushability of the catheter 130 to enable the catheter 130 to be navigated through the vasculature without the aid of a guide device (e.g., a guidewire or a guide catheter). In other examples, the user may use an introducer catheter, guide catheter, or needle within which the flexible catheter 130 may be inserted to the target location. Alternatively, or additionally, the user may insert a guidewire (e.g., guidewire 182) to navigate the flexible catheter 170 to the target location and then slide flexible catheter 170 over the guidewire and remove the guidewire prior to delivering the medical adhesive 186, as discussed with respect to FIGS. 10A and 10B.

Once the flexible catheter 130 is positioned at the target location, the user may insert the pre-filled cartridge 144 that includes medical adhesive 98 into the flexible catheter 130 (222). Then, the user may advance the shaft 152 through at least a portion of lumen 133 of the flexible catheter 130 and the pre-filled cartridge 144 to force at least a first portion of the volume of medical adhesive 98 (e.g., a bolus) out of distal opening 150 of the pre-filled cartridge 144 and the distal end of the flexible catheter 130 (224). The user may then apply pressure to the tissue above the target location that received the first portion of medical adhesive to collapse the vein and set the medical adhesive (226). If there is another target location within then vein ("YES" branch of block 228), the user may withdraw the flexible catheter 130 and position the distal end of the flexible catheter 130 at the new target location (230). The user may then advance the shaft 152 further through lumen 133 and the pre-filled cartridge 144 in order to deliver a second portion of the volume of medical adhesive 98 to the section target location of the vessel (224). This process may be repeated until the entire length of the vessel has been coapted with medical adhesive 98. If there is no other target area to be treated by medical adhesive 98 ("NO" branch of block 228), the user may remove the flexible catheter 130 and the shaft 152 (e.g., part of the mandrel) from the patient (232).

In some examples, the volume of medical adhesive 98 delivered from the pre-filled cartridge 144 may be within a range from approximately 1.0 mL to approximately 4.0 mL. This volume may be different for the treatment of different vessels. For example, treatment of the greater saphenous vein may require a larger volume of medical adhesive than treatment of a perforator vein. Therefore, pre-filled cartridges with different volumes of medical adhesive may be available for treatment of certain vessels. These different available volumes of the pre-filled cartridge 144 may reduce medical adhesive waste for smaller vessels or smaller treatment areas. In addition, in some examples in which all of medical adhesive 98 has been delivered but more target locations still need to be treated, the user may remove the shaft 152 from lumen 133 and insert a new the pre-filled cartridge 144 with medical adhesive into the flexible catheter 130 prior again advancing the shaft 152 (223).

Various examples have been described. These and other examples are within the scope of the following claims.

What is claimed is:

1. A medical assembly comprising:
a flexible catheter configured to be disposed within a hollow anatomical structure of a patient, wherein an inner wall of the flexible catheter defines a lumen having a lumen cross-sectional dimension and a distal opening of the lumen, and wherein the lumen is configured to contain a volume of medical adhesive; and
a shaft defining a shaft cross-sectional dimension smaller than the lumen cross-sectional dimension of at least a portion of the lumen, wherein the shaft defines a distal surface configured to contact the medical adhesive in the lumen of the flexible catheter, wherein advancement of the shaft through at least a portion of the lumen and contact of at least a portion of the shaft with the inner wall causes the distal surface of the shaft to apply pressure to the medical adhesive which forces at least a portion of the volume of medical adhesive out of the distal opening of the lumen, and wherein:
the portion of the lumen is a first portion of the lumen,
the lumen cross-sectional dimension is a first lumen cross-sectional dimension of the first portion of the lumen,
the flexible catheter comprises a proximal end that defines the first portion of the lumen, and
the flexible catheter comprises a distal end that defines the distal opening and a second portion of the lumen having a second lumen cross-sectional dimension smaller than the first lumen cross-sectional dimension and smaller than the shaft cross-sectional dimension.

2. The medical assembly of claim 1, further comprising the volume of medical adhesive pre-filled within the lumen of the flexible catheter.

3. The medical assembly of claim 2, wherein the medical adhesive has a viscosity between approximately 8,000 centipoise (cps) and 12,000 cps.

4. The medical assembly of claim 1, wherein the shaft cross-sectional dimension is sized to be less than the lumen cross-sectional dimension of the lumen and prevent the volume of medical adhesive from flowing between the shaft and a wall of the flexible catheter.

5. The medical assembly of claim 1, wherein the flexible catheter defines a side opening configured to be disposed distal to the volume of the medical adhesive pre-filled within the lumen, the side opening being configured to receive a guidewire.

6. The medical assembly of claim 5, wherein the flexible catheter comprises a flap configured to move between a first position that retains the volume of the medical adhesive proximal to the side opening and a second position that closes the side opening from the lumen, wherein advancement of the medical adhesive distally within the lumen forces the flap from the first position to the second position.

7. The medical assembly of claim 1, further comprising a pre-filled cartridge filled with the volume of the medical adhesive, wherein the pre-filled cartridge is configured to be inserted into the lumen.

8. The medical assembly of claim 7, wherein the pre-filled cartridge defines an outer diameter that is less than the lumen cross-sectional dimension.

9. The medical assembly of claim 7, wherein the flexible catheter defines a side opening configured to receive a guidewire.

10. The medical assembly of claim 9, wherein advancement of the pre-filled cartridge distal to the side opening closes the side opening.

11. The medical assembly of claim 9, wherein the flexible catheter comprises a flap configured to move between a first position that enables the guide wire to enter the side opening and a second position that closes the side opening from the lumen, wherein advancement of the pre-filled cartridge distally within the lumen forces the flap from the first position to the second position.

12. The medical assembly of claim 1, wherein the lumen cross-sectional dimension comprises a diameter in a range of approximately 0.102 centimeters (cm) to approximately 0.254 cm.

13. The medical assembly of claim 1, wherein an external diameter of the flexible catheter is in a range of approximately 0.114 cm to approximately 0.292 cm.

14. The medical assembly of claim 1, wherein the flexible catheter comprises a reinforced section comprising at least one of a coil or a braid within a wall of the flexible catheter.

15. The medical assembly of claim 1, wherein the flexible catheter comprises an echogenic portion at a distal portion of the flexible catheter.

16. The medical assembly of claim 1, wherein the flexible catheter comprises a polytetrafluoroethylene liner that defines the lumen.

17. The medical assembly of claim 1, wherein the volume of the medical adhesive is within a range from approximately 1.0 mL to approximately 4.0 mL.

18. The medical assembly of claim 1, wherein the flexible catheter comprises one of a flap or a breakable cover configured to cover a distal end of the flexible catheter, wherein the pressure applied to the medical adhesive forces the flap or breakable cover open to enable at least the portion of the volume of medical adhesive out of the distal opening of the lumen.

19. A method comprising:
navigating a distal end of a flexible catheter to a target location within a hollow anatomical structure of a patient, wherein an inner wall of the flexible catheter defines a lumen having a lumen cross-sectional dimension, and a distal opening of the lumen, and wherein the lumen is configured to contain a volume of medical adhesive; and
advancing a shaft through at least a portion of the lumen, wherein the shaft defines a distal surface configured to contact the medical adhesive in the lumen of the flexible catheter, and wherein advancement of the shaft through at least the portion of the lumen and contact of at least a portion of the shaft with the inner wall causes the distal surface of the shaft to apply pressure to the medical adhesive which forces at least a portion of the volume of the medical adhesive out of the distal opening of the lumen, wherein the shaft defines a shaft cross-sectional dimension smaller than the lumen cross-sectional dimension of at least a portion of the lumen, and wherein:

the portion of the lumen is a first portion of the lumen,
the lumen cross-sectional dimension is a first lumen cross-sectional dimension of the first portion of the lumen,
the flexible catheter comprises a proximal end that defines the first portion of the lumen, and
the flexible catheter comprises a distal end that defines the distal opening and a second portion of the lumen having a second lumen cross-sectional dimension smaller than the first lumen cross-sectional dimension and smaller than the shaft cross-sectional dimension.

20. The method of claim 19, wherein the lumen of the flexible catheter is pre-filled with the volume of the medical adhesive prior to navigating the distal end of the flexible catheter to the target location.

21. The method of claim 20, further comprising inserting a guidewire through a side opening defined by the flexible catheter, the side opening being distal to the volume of medical adhesive.

22. The method of claim 21, further comprising withdrawing the guidewire from the side opening and the lumen, wherein advancing the shaft causes the medical adhesive within the lumen to force a flap of the flexible catheter to move from a first position that retains the volume of the medical adhesive proximal to the side opening to a second position that closes the side opening from the lumen.

23. The method of claim 19, further comprising inserting a pre-filled cartridge filled with the volume of the medical adhesive into the lumen of the flexible catheter.

24. The method of claim 23, wherein advancing the shaft through at least the portion of the lumen comprises advancing the shaft through a proximal portion of the pre-filled cartridge to force at least a portion of the medical adhesive out of a distal end of the pre-filled cartridge and out of the distal opening of the lumen of the flexible catheter.

25. The method of claim 19, wherein the lumen cross-sectional dimension comprises a diameter in a range of approximately 0.102 cm to approximately 0.254 cm.

26. The method of claim 19, wherein the at least the portion of the volume of the medical adhesive comprises a first portion of the volume of the medical adhesive, and wherein the method further comprises:
subsequent to advancing the shaft to force the first portion of the volume of the medical adhesive out of the distal opening of the lumen, withdrawing the distal end of the flexible catheter to a second location within the hollow anatomical structure; and
advancing the shaft through the lumen to force a second portion of the volume of the medical adhesive out of the distal opening of the lumen at the second location.

27. The method of claim 19, wherein the volume of the medical adhesive is within a range from approximately 1.0 mL to approximately 4.0 mL.

28. A medical assembly comprising:
a flexible catheter configured to be disposed within a hollow anatomical structure of a patient, wherein:
an inner wall of the flexible catheter defines a lumen having a lumen cross-sectional dimension and a distal opening of the lumen, the lumen cross-sectional dimension comprising a range of approximately 0.102 cm to approximately 0.254 cm,
the flexible catheter comprises a reinforced section comprising at least one of a coil or a braid within a wall of the flexible catheter,
the lumen is configured to contain a volume of medical adhesive pre-filled within the lumen, and
the flexible catheter defines a side opening configured to be disposed distal to the volume of the medical adhesive pre-filled within the lumen, the side opening being configured to receive a guidewire; and
a shaft defining a shaft cross-sectional dimension smaller than the lumen cross-sectional dimension at least a portion of the lumen, wherein the shaft defines a distal surface configured to contact the medical adhesive in the lumen of the flexible catheter, and wherein advancement of the shaft through at least a portion of the lumen and contact of at least a portion of the shaft with the inner wall causes the distal surface of the shaft to apply pressure to the medical adhesive which forces at least a portion of the volume of medical adhesive out of the distal opening of the lumen of the flexible catheter, wherein the volume of the medical adhesive is within a range from approximately 1.0 mL to approximately 4.0 mL.

29. The medical assembly of claim 28, wherein the portion of the lumen is a first portion of the lumen, wherein the lumen cross-sectional dimension is a first lumen cross-sectional dimension of the first portion of the lumen, wherein the flexible catheter comprises a proximal end that defines the first portion of the lumen, and wherein the flexible catheter comprises a distal end that defines the distal opening and a second portion of the lumen having a second lumen cross-sectional dimension smaller than the first lumen cross-sectional dimension and smaller than the shaft cross-sectional dimension.

* * * * *